US012691293B2

(12) United States Patent
Otteson et al.

(10) Patent No.: US 12,691,293 B2
(45) Date of Patent: Jul. 28, 2026

(54) TEMPERATURE SENSORS IN MEDICAL IMPLANTS

(71) Applicant: Medtronic, Inc., Minneapolis, MN (US)

(72) Inventors: Brett Otteson, Minneapolis, MN (US); Venkat R. Gaddam, Plymouth, MN (US); Yohan Kim, Fridley, MN (US); Boysie R. Morgan, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 1144 days.

(21) Appl. No.: 17/646,835

(22) Filed: Jan. 3, 2022

(65) Prior Publication Data

US 2022/0212017 A1 Jul. 7, 2022

Related U.S. Application Data

(60) Provisional application No. 63/134,436, filed on Jan. 6, 2021.

(51) Int. Cl.
*A61N 1/378* (2006.01)
*H02J 50/10* (2016.01)

(52) U.S. Cl.
CPC ............ *A61N 1/3787* (2013.01); *H02J 50/10* (2016.02)

(58) Field of Classification Search
CPC ....... A61B 5/02055; A61B 5/01; A61B 5/686; A61N 1/378; A61N 1/3605; A61N 1/36142; H02J 50/10; H02J 7/00309; H02J 2310/23
See application file for complete search history.

(56) References Cited

U.S. PATENT DOCUMENTS

| | | | |
|---|---|---|---|
| 6,681,135 B1 | 1/2004 | Davis et al. | |
| 6,736,770 B2 | 5/2004 | Eysieffer et al. | |
| 8,326,426 B2 | 12/2012 | Thornton et al. | |
| 8,380,311 B2 | 2/2013 | Li et al. | |
| 9,142,989 B2 | 9/2015 | Fell et al. | |

(Continued)

OTHER PUBLICATIONS

Aldridge, Clare. "Lee Spring Draws Attention to the When and Why of Plastic Springs." FastFixTechnology.Com, Aug. 28, 2019, fastfixtechnology.com/automotive/lee-spring-draws-attention-to-the-when-and-why-of-plastic-springs/. (Year: 2019).*

(Continued)

*Primary Examiner* — Adam J Eiseman
*Assistant Examiner* — Lucy Eppert
(74) *Attorney, Agent, or Firm* — Shumaker & Sieffert, P.A.

(57) ABSTRACT

Devices, systems, and techniques for monitoring the temperature of a device such as an implantable medical device is disclosed. An implantable medical device includes a housing with at least one support disposed within the housing, a temperature sensor thermally coupled to the interior surface of the housing, wherein the temperature sensor is disposed within the housing and configured to sense a temperature of a portion of the housing. At least one physically compliant material is disposed between the at least one support and the temperature sensor, where the physically compliant material is configured to provide a physical bias against the temperature sensor and towards the interior surface of the housing.

18 Claims, 13 Drawing Sheets

(56)  References Cited

U.S. PATENT DOCUMENTS

| | | | |
|---|---|---|---|
| 9,151,811 | B2 | 10/2015 | Jester et al. |
| 9,270,134 | B2 | 2/2016 | Gaddam et al. |
| 9,719,867 | B2 | 8/2017 | Sharratt et al. |
| 9,789,325 | B2 | 10/2017 | Shelton et al. |
| 9,981,137 | B2 | 5/2018 | Eiger |
| 10,258,804 | B2 | 4/2019 | Scott et al. |
| 10,502,638 | B2 | 12/2019 | Miura et al. |
| 10,554,069 | B2 | 2/2020 | Paralikar et al. |
| 2002/0051550 | A1 | 5/2002 | Leysieffer |
| 2013/0278226 | A1* | 10/2013 | Cong ........................ G01J 5/07 |
| | | | 320/150 |
| 2017/0131156 | A1 | 5/2017 | Miura et al. |
| 2019/0060656 | A1 | 2/2019 | Scott et al. |

OTHER PUBLICATIONS

Rabin et al., "Test methods for integrated experimental prototypes of wireless charing of implants' power supply sources and implantable biotelemetric system," IOP Conference Series: Earth and Environmental Science, vol. 315, Issue 3, 032033, doi:10.1088/1755-1315/315/3/032033, Aug. 23, 2019, 9 pp.

* cited by examiner

302 ATTACH COMPLIANT PAD TO SUPPORT

304 ATTACH TEMPERATURE SENSOR TO COMPLIANT PAD

306 THERMALLY COUPLE TEMPERATURE SENSOR TO HOUSING

TEMPERATURE SENSORS IN MEDICAL IMPLANTS

This application claims the benefit of U.S. Provisional Patent Application No. 63/134,436, filed Jan. 6, 2021, the entire contents of which is incorporated herein by reference.

TECHNICAL FIELD

The disclosure relates to medical devices and, more particularly, temperature sensors for sensing temperature of implantable medical devices.

BACKGROUND

Implantable medical devices (IMDs) may be used to monitor a patient condition and/or deliver therapy to the patient. In long term or chronic uses, IMDs may include a rechargeable power source (e.g., comprising one or more capacitors or batteries) that extends the operational life of the medical device to weeks, months, or even years over a non-rechargeable device.

When the energy stored in the rechargeable power source has been depleted, the patient may use an external charging device to recharge the power source. Since the rechargeable power source is implanted in the patient and the charging device is external to the patient, this charging process may be referred to as transcutaneous charging. In some examples, transcutaneous charging may be performed via inductive coupling between a primary coil in the charging device and a secondary coil in the IMD.

When a current is applied to the primary coil and the primary coil is aligned with the secondary coil, electrical current is induced in the secondary coil within the patient. Circuitry associated with the IMD uses the current to charge a rechargeable power source, such as a battery, within the IMD. Therefore, the external charging device does not need to physically connect with the rechargeable power source for charging to occur.

SUMMARY

In general, the disclosure is directed to devices, systems, and techniques for monitoring the temperature of a medical device, e.g., monitoring the temperature as feedback for controlling charging of a rechargeable power source, general operation of the device, or indication of malfunctioning components. An implantable medical device (IMD) may include a rechargeable power source that can be transcutaneously charged. The IMD, an external charging device, or other medical device associated with charging the rechargeable power source may include a temperature sensor that monitors the temperature of the respective device (e.g., the IMD, external charging device, or other medical device) during a charging session. Since recharging may be limited by the temperature of the housing of the IMD to reduce a risk of unwanted heating of tissue, one or more components of the system may monitor the temperature of the device to control charging of the rechargeable power source and avoid exposing patient tissue to undesirable temperatures.

The temperature sensor may be configured to sense the temperature of a portion of the device being monitored while being thermally-coupled to this portion of the device being monitored for temperature changes. In other words, the temperature sensor may utilize indirect temperature measurement techniques to sense the temperature of a particular surface or material within a device.

In one or more examples, the disclosure is directed to an implantable device that includes a medical device comprising a housing. A temperature sensor may be disposed within the housing and configured to sense a temperature of a portion of the medical device, wherein the temperature sensor is configured to be thermally coupled to the portion. At least one processor may be configured to control charging of a rechargeable power source based on the sensed temperature. In one example, the disclosure describes an implantable medical device may include a housing with at least one support disposed within the housing, and a temperature sensor thermally coupled to the interior surface of the housing, wherein the temperature sensor is disposed within the housing and configured to sense a temperature of a portion of the housing. At least one physically compliant material is disposed between the at least one support and the temperature sensor, where the physically compliant material is configured to provide a physical bias against the temperature sensor and towards the interior surface of the housing.

In one example, a method includes disposing a temperature sensor within a housing, the housing comprising an exterior surface and an interior surface, the housing having at least one support coupled to the housing, disposing at least one physically compliant material between the at least one support and the temperature sensor, where the at least one physically compliant material is configured to physically bias the temperature sensor towards the interior surface of the housing with the physically compliant material, and thermally coupling the temperature sensor to the housing, the temperature sensor configured to sense a temperature of a portion of the housing, the temperature sensor including a sensor surface.

In one example, the disclosure describes an implantable medical device may include a housing with at least one support disposed within the housing, and a temperature sensor thermally coupled to the interior surface of the housing, wherein the temperature sensor is disposed within the housing and configured to sense a temperature of a portion of the housing. At least one physically compliant material is disposed between the at least one support and the temperature sensor, where the physically compliant material is configured to provide a physical bias against the temperature sensor and towards the interior surface of the housing. A hybrid board may be disposed within the housing, where a flexible circuit may electrically couple the temperature sensor to the hybrid board, and processing circuitry may be configured to receive a temperature signal from the temperature sensor and control at least one function of the implantable medical device based on the temperature signal.

The details of one or more example are set forth in the accompanying drawings and the description below. Other features, objects, and advantages will be apparent from the description and drawings, and from the claims.

DETAILED DESCRIPTION

Figure 1:
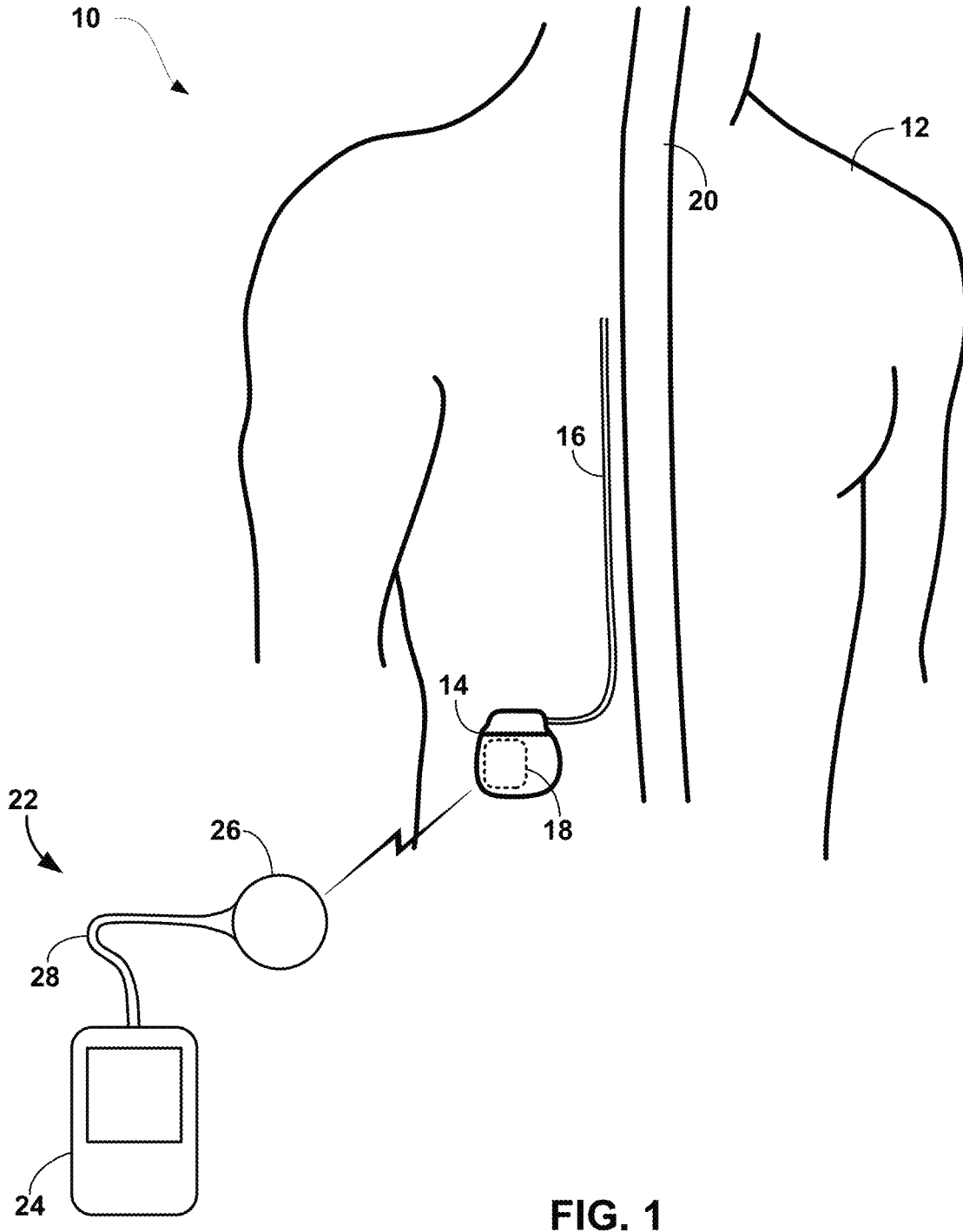
FIG. 1 is a conceptual diagram illustrating an example system that includes an implantable medical device (IMD) and an external charging device that charges a rechargeable power source of the IMD.

This disclosure is generally directed to devices, systems, and techniques for sensing a temperature of a portion of a medical device, such as the housing of the medical device. Since medical devices come into contact with human tissue, it may be beneficial to monitor the temperature of the medical device over time and/or during certain events. Some medical devices can determine temperature or heat based on indirect measurements of power used within the medical device and/or power applied to the medical during wireless recharge, for example. However, these indirect measurements may not be an accurate representation of the temperature of the medical device or the temperate at a certain location on or within the medical device. In other medical devices, a circuit board may include a temperature sensor that senses the temperature of the medical device at that position on the circuit board. However, the temperature sensed at the circuit board may not be indicative of the temperatures of the housing of the medical device or other external surfaces of the medical device that contact patient tissue. Placement of a temperature sensor in contact with a desired portion of a housing provides packaging and manufacturing challenges for a medical device, but more accurate measurements of certain portions of the medical device may provide operational and safety benefits.

Implantable medical devices (IMDs) may be implanted within a patient and used to monitor a parameter of the patient and/or deliver a therapy to the patient. To extend the operational life of the IMD, the IMD may include a rechargeable power source (e.g., one or more capacitors or batteries). When the rechargeable power source is being recharged, the power transmitted to the IMD generates heat via increased current to the battery and eddy currents on the housing, for example, that increases the temperature of the IMD. In addition, an external charging device (e.g., another medical device) placed against the skin of the patient may increase in temperature when power is transmitted during the recharging session. Higher charging power may reduce charging times while also increasing heating of the IMD. This may result in heating of tissue proximate the IMD and/or proximate the external charging device. In order to prevent undesirable temperatures, the system may monitor sensed temperatures in the IMD and/or external charging device. Without accurate temperature sensing, the system may be conservative with high power recharge to reduce the risk of undesirable high temperature. Therefore, accurate temperature sensing of one or more portions of the IMD or other device associated with charging may reduce recharge times and increase patient comfort.

As described herein, a medical device may include one or more temperature sensors thermally coupled to target portions of the medical device. Using the sensed temperature, a system can monitor the temperature the specific portions of the device, such as the temperatures occurring during recharge of a rechargeable power source within the medical device. An IMD may include a housing and a temperature sensor, in one or more examples, physically attached and/or thermally coupled to the surface of the housing within the IMD. For example, the one or more sensors may be positioned between a mounting structure and an inner surface of the housing. One or more compliant materials may be configured to provide a bias to the temperature sensor in order to maintain the thermal coupling between the temperature sensor and the housing.

The IMD or other device associated with charging may use the output from one or more temperature sensors as feedback for controlling the charging of the implanted rechargeable power source. The IMD and/or external charging device may thus monitor one or more temperatures to control charging and effectively limit temperatures of patient tissue adjacent the IMD and/or external charging device. For example, one or more processors (e.g., processing circuitry) may reduce the power used during the charging session, cycle the power to control heat imparted to tissue (e.g., cycle it on and off), or terminate the charging session in response to a temperature exceeding a threshold. In other examples, the IMD or other device may employ the temperature sensed by a temperature sensor to perform other or additional functions. For example, a processor may compare the sensed temperature to a fault condition threshold and disconnect the rechargeable power source from at least one electrical circuit when the sensed temperature exceeds the fault condition threshold. By including temperature sensors thermally coupled to the target structure of the medical device, such as the inner surface of the housing, the IMD or other device may receive accurate temperature information to precisely control charging power during a recharge session.

FIG. 1 is a conceptual diagram illustrating an example system 10 that includes implantable medical device (IMD) 14 and external charging device 22 that charges rechargeable power source 18 of IMD 14. Although the techniques described in this disclosure are generally applicable to a variety of medical devices including medical devices such as patient monitors, electrical stimulators, or drug delivery devices, application of such techniques to implantable neurostimulators will be described for purposes of illustration. More particularly, the disclosure will refer to an implantable neurostimulation system for use in spinal cord stimulation therapy, but without limitation as to other types of medical devices. In other examples, temperature sensors may be included in other non-medical devices such as personal electronics, mechanical devices, or any other type of structure.

As shown in FIG. 1, system 10 includes an IMD 14 and external charging device 22 shown in conjunction with a patient 12, who is ordinarily a human patient. In the example of FIG. 1, IMD 14 is an implantable electrical stimulator that delivers neurostimulation therapy to patient 12, e.g., for relief of chronic pain or other symptoms. Generally, IMD 14 may be a chronic electrical stimulator that remains implanted within patient 12 for weeks, months, or even years. In the example of FIG. 1, IMD 14 and lead 16 may be directed to delivering spinal cord stimulation therapy. In other examples, IMD 14 may be a temporary, or trial, stimulator used to screen or evaluate the efficacy of electrical stimulation for chronic therapy. IMD 14 may be implanted in a subcutaneous tissue pocket, within one or more layers of muscle, or other internal location. IMD 14 includes rechargeable power source 18, such as a rechargeable battery, and IMD 14 is coupled to lead 16.

Electrical stimulation energy, which may be constant current or constant voltage based pulses, for example, is delivered from IMD 14 to one or more targeted locations within patient 12 via one or more electrodes (not shown) of lead 16. The parameters for a program that controls delivery of stimulation energy by IMD 14 may include information identifying which electrodes have been selected for delivery of stimulation according to a stimulation program, the polarities of the selected electrodes, i.e., the electrode configuration for the program, and voltage or current amplitude, pulse rate, pulse shape, and pulse width of stimulation delivered by the electrodes. Electrical stimulation may be delivered in the form of stimulation pulses or continuous waveforms, for example.

In the example of FIG. 1, lead 16 is disposed within patient 12, e.g., implanted within patient 12. Lead 16 tunnels through tissue of patient 12 from along spinal cord 20 to a subcutaneous tissue pocket or other internal location where IMD 14 is disposed. Although lead 16 may be a single lead, lead 16 may include a lead extension or other segments that may aid in implantation or positioning of lead 16. In addition, a proximal end of lead 16 may include a connector (not shown) that electrically couples to a header of IMD 14. Although only one lead 16 is shown in FIG. 1, system 10 may include two or more leads, each coupled to IMD 14 and directed to similar or different target tissue sites. For example, multiple leads may be disposed along spinal cord 20 or leads may be directed to spinal cord 20 and/or other locations within patient 12.

Lead 16 may carry one or more electrodes that are placed adjacent to the target tissue, e.g., spinal cord 20 for spinal cord stimulation (SCS) therapy. One or more electrodes may be disposed at a distal tip of lead 16 and/or at other positions at intermediate points along lead 16, for example. Electrodes of lead 16 transfer electrical stimulation generated by an electrical stimulation generator in IMD 14 to tissue of patient 12. The electrodes may be electrode pads on a paddle lead, circular (e.g., ring) electrodes surrounding the body of the lead, conformable electrodes, cuff electrodes, segmented electrodes, or any other type of electrodes capable of forming unipolar, bipolar or multipolar electrode configurations for therapy. In general, ring electrodes arranged at different axial positions at the distal ends of lead 16 will be described for purposes of illustration.

In alternative examples, lead 16 may be configured to deliver stimulation energy generated by IMD 14 to stimulate one or more sacral nerves of patient 12, e.g., sacral nerve stimulation (SNS). SNS may be used to treat patients suffering from any number of pelvic floor disorders such as pain, urinary incontinence, fecal incontinence, sexual dysfunction, or other disorders treatable by targeting one or more sacral nerves. Lead 16 and IMD 14 may also be configured to provide other types of electrical stimulation or drug therapy (e.g., with lead 16 configured as a catheter). For example, lead 16 may be configured to provide deep brain stimulation (DBS), peripheral nerve stimulation (PNS), gastric stimulation to treat obesity or gastroparesis, tibial nerve stimulation, or other deep tissue or more superficial types of electrical stimulation. In other examples, lead 16 may provide one or more sensors configured to allow IMD 14 to monitor one or more parameters of patient 12. The one or more sensors may be provided in addition to, or in place of, therapy delivery by lead 16.

IMD 14 delivers electrical stimulation therapy to patient 12 via selected combinations of electrodes carried by lead 16. The target tissue for the electrical stimulation therapy may be any tissue affected by electrical stimulation energy, which may be in the form of electrical stimulation pulses or waveforms. In some examples, the target tissue includes nerves, smooth muscle, and skeletal muscle. In the example illustrated by FIG. 1, the target tissue for electrical stimulation delivered via lead 16 is tissue proximate spinal cord 20 (e.g., one or more target locations of the dorsal columns or one or more dorsal roots that branch from spinal cord 20. Lead 16 may be introduced into spinal cord 20 via any suitable region, such as the thoracic, cervical or lumbar regions. Stimulation of dorsal columns, dorsal roots, and/or peripheral nerves may, for example, prevent pain signals from traveling through spinal cord 20 and to the brain of the patient. Patient 12 may perceive the interruption of pain signals as a reduction in pain and, therefore, efficacious therapy results. For treatment of other disorders, lead 16 may be introduced at any exterior location of patient 12.

Although lead 16 is described as generally delivering or transmitting electrical stimulation signals, lead 16 may additionally or alternatively transmit electrical signals from patient 12 to IMD 14 for monitoring. For example, IMD 14 may utilize detected nerve impulses to diagnose the condition of patient 12 or adjust the delivered stimulation therapy. Lead 16 may thus transmit electrical signals to and from patient 12.

A user, such as a clinician or patient 12, may interact with a user interface of an external programmer (not shown) to program IMD 14. Programming of IMD 14 may refer generally to the generation and transfer of commands, programs, or other information to control the operation of IMD 14. For example, the external programmer may transmit programs, parameter adjustments, program selections, group selections, or other information to control the operation of IMD 14, e.g., by wireless telemetry or wired connection.

In some cases, an external programmer may be characterized as a physician or clinician programmer if it is primarily intended for use by a physician or clinician. In other cases, the external programmer may be characterized as a patient programmer if it is primarily intended for use by a patient. A patient programmer is generally accessible to patient 12 and, in many cases, may be a portable device that may accompany the patient throughout the patient's daily routine. In general, a physician or clinician programmer may support selection and generation of programs by a clinician for use by stimulator 14, whereas a patient programmer may support adjustment and selection of such programs by a patient during ordinary use. In other examples, external charging device 22 may be included with, or form part of, an external programmer. In this manner, a user such as a clinician, other caregiver, or patient may program and charge IMD 14 using one device, or multiple devices.

IMD 14 may be constructed of any polymer, metal, or composite material sufficient to house the components of IMD 14 (e.g., components illustrated in FIG. 2) within patient 12. In this example, IMD 14 may be constructed with a biocompatible housing, such as titanium or stainless steel, or a polymeric material such as silicone or polyurethane, and surgically implanted at a site in patient 12 near the pelvis, abdomen, or buttocks. The housing of IMD 14 may be configured to provide a hermetic seal for components, such as rechargeable power source 18. In addition, the housing of IMD 14 may be selected of a material that facilitates receiving energy to charge rechargeable power source 18.

As described herein, rechargeable power source 18 may be included within IMD 14. However, in other examples, rechargeable power source 18 could be located external to a housing of IMD 14, separately protected from fluids of patient 12, and electrically coupled to electrical components of IMD 14. This type of configuration of IMD 14 and rechargeable power source 18 may provide implant location flexibility when anatomical space for implantable devices is minimal. In any case, rechargeable power source 18 may provide operational electrical power to one or more components of IMD 14.

Rechargeable power source 18 may include one or more capacitors, batteries, or components (e.g. chemical or electrical energy storage devices). Example batteries may include lithium-based batteries, nickel metal-hydride batteries, or other materials. Rechargeable power source 18 is also rechargeable. In other words, rechargeable power source 18 may be replenished, refilled, or otherwise capable of increasing the amount of energy stored after energy has been depleted. Rechargeable power source 18 may be subjected to numerous discharge and recharge cycles (e.g., hundreds or even thousands of cycles) over the life of rechargeable power source 18 in IMD 14. Rechargeable power source 18 may be recharged when fully depleted or partially depleted.

Charging device 22 may be used to recharge rechargeable power source 18 and IMD 14 when implanted in patient 12. Charging device 22 may be a hand-held device, a portable device, or a stationary charging system. In any case, charging device 22 may include components necessary to charge rechargeable power source 18 through tissue of patient 12. For example, charging device 22 may include housing 24, charging cable 28, and charging head 26. Housing 24 may enclose or house at least some of the operational components of charging device 22. For example, housing 24 may include a user interface, processor, memory, power source, and other components. Charging cable 28 may electrically couple charging head 26 to the power source within housing 24, such that charging cable 28 is configured to transmit power and/or information to charging head 26. Charging head 26 may include a coil (e.g., a component of charging head 26) for inductive coupling or components used to transmit power from charging head 26 to rechargeable power source 18. In other examples, charging cable 28 and/or charging head 26 may also be contained within or disposed on housing 24, or various ones of the components associated with charging device 22 may be carried by cable 28 and/or charging head 26. Although a user may control the recharging process with a user interface of charging device 22, charging device may alternatively be controlled by another device (e.g., an external programmer).

In some examples, charging device 22 may only perform charging of rechargeable power source 18. In other examples, charging device 22 may be an external programmer or other device configured to perform additional functions. For example, when embodied as an external programmer, charging device 22 may transmit programming commands to IMD 14 in addition to charge rechargeable power source 18. In another example, charging device 22 may communicate with IMD 14 to transmit and/or receive information related to the charging of rechargeable power source 18. For example, IMD 14 may transmit information regarding temperature of IMD 14 and/or rechargeable power source 18, received power during charging, the charge level of rechargeable power source 18, charge depletion rates during use, or any other information related to power consumption and recharging of IMD 14 and rechargeable power source 18.

Charging device 22 and IMD 14 may utilize any wireless power transfer techniques that are capable of recharging rechargeable power source 18 of IMD 14 when IMD 14 is implanted within patient 14. In one example, system 10 may utilize inductive coupling between a coil of charging device 22 (e.g., a coil within charging head 26) and a coil of IMD 14 coupled to rechargeable power source 18. In inductive coupling, charging device 22 is placed near implanted IMD 14 such that a primary coil of charging device 22 is aligned with, i.e., placed over, a secondary coil of IMD 14. Charging device 22 may then generate an electrical current in the primary coil based on a selected power level for charging rechargeable power source 18. As described further below, the power level may be selected to control the temperature of IMD 14 and/or the charge rate of rechargeable power source 18. When the primary and secondary coils are aligned, the electrical current in the primary coil may magnetically induce an electrical current in the secondary coil within IMD 14. Since the secondary coil is associated with and electrically coupled to rechargeable power source 18, the induced electrical current may be used to increase the voltage, or charge level, of rechargeable power source 18. Although inductive coupling is generally described herein, any type of wireless energy transfer may be used to charge rechargeable power source 18.

During the energy transfer process that charges rechargeable power source 18, some of the energy involved in the charging process may be converted into heat at rechargeable power source 18, other components of IMD 14, and/or in charging head 26, for example. When increased energy levels are used to charge rechargeable power source 18 at a higher rate, the temperature of IMD 14 and/or charging device 22 may also increase. Although the temperature of the IMD 14 housing may not achieve a temperature sufficient to burn or necrose tissue adjacent to the housing of IMD 14, elevated temperatures may be undesirable and could cause discomfort in some cases. Therefore, one or more devices may monitor temperatures of any device or component that may come into contact with or otherwise affect tissue of patient 12. The sensed temperature may be used as feedback in a closed-loop or partially closed-loop temperature control system. For example, charging device 22 may control the power level, power cycle times, and/or charging time used to charge rechargeable power source 18 to reduce or minimize any undesirable temperatures of IMD 14 that could be caused by charging rechargeable power source 18. In addition, monitoring the temperature of IMD 14 and/or the temperature of tissue adjacent to the housing of IMD 14 may minimize patient discomfort during the charging process and reduce the amount of time to recharge the IMD.

As described herein, system 10 may utilize one or more temperature sensors to sense, measure, or otherwise detect the temperature of a portion of a device. In one example, a temperature sensor of system 10 may sense the temperature of a portion of a medical device (e.g., charging head 26 or IMD 14). A processor of system 10 (e.g., a processor housed by either charging device 22 or IMD 14) may be configured to control charging of rechargeable power source 18 based on the sensed temperature. In this manner, the temperature sensor may provide feedback for controlling the charging of rechargeable power source 18. For example, charging device 22 may control current applied to a primary coil within charging head 26 based on the sensed temperature. Charging device 22 may control current, for example, by controlling a current amplitude, duty cycle, or other characteristic of the charging current. In some examples, the temperature sensor may be disposed within a housing of the medical device (e.g., a housing of charging head 26, housing 24, or a housing of IMD 14). In this manner, the temperature sensor may be disposed in a medical device that is either external to patient 12 or implanted within patient 12. In one or more examples, processing circuitry may be configured to receive a temperature signal from the temperature sensor and may control at least one function of the implantable medical device based on the temperature signal.

Temperature sensors described herein may take different forms and utilize different temperature sensing techniques. In one example, the temperature sensor is a top-sensing temperature sensor that is thermally coupled to the inside surface of the IMD housing.

System 10 may utilize one or more temperature sensors in one or more medical device. For example, each of charging head 26 and IMD 14 may include a single temperature sensor. In another example, each of charging head 26 (e.g., external of patient 12) and/or IMD 14 (e.g., implanted within patient 12) may include two or more temperature sensors. Multiple temperature sensors within the same device may be provided for different reasons. For example, each of the multiple temperature sensors may be oriented to sense the temperature of the same portion of the device for redundant, backup, composite, or cross-correlated temperature measurement. If multiple temperature sensors are used, the multiple sensors may be similar or may instead be sensors of different types of temperatures sensors described herein.

Alternatively, two temperature sensors may be oriented to sense temperature of different surfaces and/or components within the same device. A first temperature sensor may be configured to sense a first portion of the device and a second temperature sensor may be configured to sense a second portion of the device. The two portions may be of different components or different areas of the same component. In one example, the first portion may be a one housing surface within the device, and the second portion may be another housing surface within the device. Since temperatures within a device may be non-uniform due to component location, thermal transfer within the device, or other external factors, the multiple temperature sensors may be used to identify temperature variations or "hot spots" of the device. In some cases, a one or multi-dimension array of temperature sensors may be provided to sense one or more portions of the IMD 14 or external device (e.g., recharger).

In some examples, two surfaces being sensed for temperature may be located adjacent to one another (e.g., different locations of a generally planar surface). In this example, two temperature sensors may be mounted to the same interior surface of the IMD housing. In other examples, the two surfaces may be generally opposed to one another (e.g., two different interior surfaces of the IMD housing and separated by the hybrid board). In this example, each temperature sensor may be mounted on opposing interior surfaces of the IMD housing such that one sensor senses temperature on one side of IMD housing and the other sensor senses temperature on the opposite side IMD housing.

Each temperature sensor may sense temperatures simultaneously such that system 10 may process multiple temperatures at the same time. Alternatively, one or more temperature sensors may be selectively enabled by one or more processors. This selective temperature sensing may reduce power consumption from unnecessary temperature sensors. In addition, selective temperature sensing may reduce power consumption and/or processing speed needed to process signals from unneeded temperature sensors.

System 10 may control the charging of rechargeable power source 18 using one or more techniques. Using the sensed temperature, a processor may compare the sensed temperature to a threshold temperature. The sensed temperature may be from a temperature sensor located within IMD 14 and/or charging device 22. The threshold temperature may be a value stored by a memory. The threshold temperature may be selected based on tissue models, patient history, or any other information that may be used to determine when a charging session should be modified. The processor may then determine when the sensed temperature exceeds the threshold temperature. When the sensed temperature exceeds the threshold temperature, the processor may control charging of rechargeable power source 18 by adjusting a power level used to charge rechargeable power source 18. In other words, the processor may reduce the power level when the temperature threshold is exceeded, turn the power off for a predetermined period of time before the power is again provided (e.g., cycle the power on and off) or even terminate the charging session. Reducing the power level may reduce the energy used to charge rechargeable power source 18 and/or the rate at which rechargeable power source 18 is recharged.

When sensing a temperature of a component of IMD 14, a processor of IMD may merely transmit the calculated temperature or data representative of the temperature to charging device 22. A processor of charging device 22 may then determine how to control the charging session. Alternatively, the processor of IMD 14 may determine how to control the charging session and transmit a respective command to charging device 22.

Charging device 22 may thus charge rechargeable power source 18 using one or more power levels or cycle times in some examples. In one example, charging device 22 may select a high power level when first starting a charging session. Charging device 22 may then select a low power level, relative to the high power level, in response to one or more temperature sensors exceeding a threshold. In this manner, the high power level may charge rechargeable power source 18 at a high rate to reduce charging time while increasing the temperature of IMD 14. Charging device 22 may select the low power level to charge rechargeable power source 18 at a slower rate to reduce the temperature of IMD 14. The low power level may be sufficiently minimal so that any increase in temperature of IMD 14 may have minimal or no effect on surrounding tissue.

A high power level and a low power level may be subjective and relative to the charging power that charging device 22 is capable of generating and transmitting to IMD 14. In some cases, the high power level may be the maximum power that charging device 22 can generate. This high power level may be referred to as a "boost" or "accelerated" charging level because of the high rate of charge induced in rechargeable power source 18. This high rate of charge may minimize the amount of time patient 12 needs to recharge rechargeable power source 18. By monitoring the temperature of one or more portions of charging head 26 and/or IMD 14, charging device 22 may charge rechargeable power source 18 with the high power level for a longer period of time without damaging tissue surrounding IMD 14.

In one example, the high power level may be approximately 2.5 Watts and the low power level may be approximately 1.0 Watt (W). Of course other power levels and ranges may be selected for use, with such levels falling either within the above-described range or outside of this range. For instance, a low power level may be much lower than 1.0 Watt in an example wherein there is good coupling between primary and second coils and wherein recharge is to be conducted relatively slowly. An example charge current level may be approximately 100 milliamps (mA) for the high power level and approximately 60 mA for the low power level. An example primary coil voltage and current for a high power may be approximately 450 V and approximately 800 mA, respectively, and an example primary coil voltage and current for a low power level may be approximately 250 V and approximately 500 mA. These values are merely examples, and other examples may include higher or lower values in accordance with the techniques described herein. In additional more than two levels may be defined (e.g., low, one or more intermediate levels, and a high level) to control charging.

In some cases, charging device 22 may cycle the driving of the primary coil. For instance, charging device 22 may drive the coil during a first period of time, and may discontinue driving the coil for a second period of time following the first period of time. This may be repeated multiple times, with the first and second time periods being selected to control an overall transmission of power (and hence heat dissipation.).

In some examples, IMD 14 may directly adjust the power level for charging (e.g., limit the charge current) instead of relying on a change in power level at charging device 22. For example, as IMD 14 receives an alternating charging current, IMD 14 may employ a circuit that may change from full-wave rectification to half-wave rectification to reduce the charge rate and temperature of IMD 14 during charging. In other words, IMD 14 may utilize half-wave rectification as a means to reduce the electrical current delivered to rechargeable power supply 18 instead of reducing the overall power received by IMD 14. Alternatively, IMD 14 may employ other mechanisms such as current and/or voltage limiters that may limit the charging rate of rechargeable power supply 18.

In other examples, a processor of charging device 22 and/or IMD 14 may perform actions other than changing a power level for charging in response to temperature changes. For example, charging device 22 may instruct a user to replace a phase change material cartridge attached to charging head 26 of charging device 22. The phase change material cartridge may act as a heat sink and increase the amount of time charging device 22 can charge rechargeable power source 18 at a high power level. In one example, a processor of charging device 22 may calculate a temperature change rate from the multiple sensed temperatures when rechargeable power source 18 is charging. The temperature change rate may be representative of how fast the temperature of charging head 26 is changing. As described above, charging head 26 may include a primary coil that transfers power wirelessly to a secondary coil within IMD 14. The processor may then determine when the temperature change rate increases subsequent to the temperature change rate decreasing during the charging. In response to determining that the temperature change rate has increased, the processor may control a user interface to present a notification that instructs a user to replace a phase change material cartridge thermally coupled to the device.

As described herein, a temperature sensor may be used to sense a temperature of a portion of IMD 14 (including rechargeable power source 18), charging head 26, and/or housing 24. A processor that controls an aspect of the charging session may be housed by IMD 14, charging head 26, or housing 24. In this manner, a processor configured to perform some or all of the functions described herein may be housed together with a temperature sensor or separate from the temperature sensor.

Although an implantable rechargeable power source 18 is generally described herein, techniques of this disclosure may also be applicable to a rechargeable power source 18 that is not implanted. For example, rechargeable power source 18 may be external to the skin of patient 12 and in physical contact with the skin. Therefore, charging device 22 may control the charging of rechargeable power source 18 with temperature sensed within charging head 26 or IMD 14 even when the power source is external to patient 12.

Figure 2:
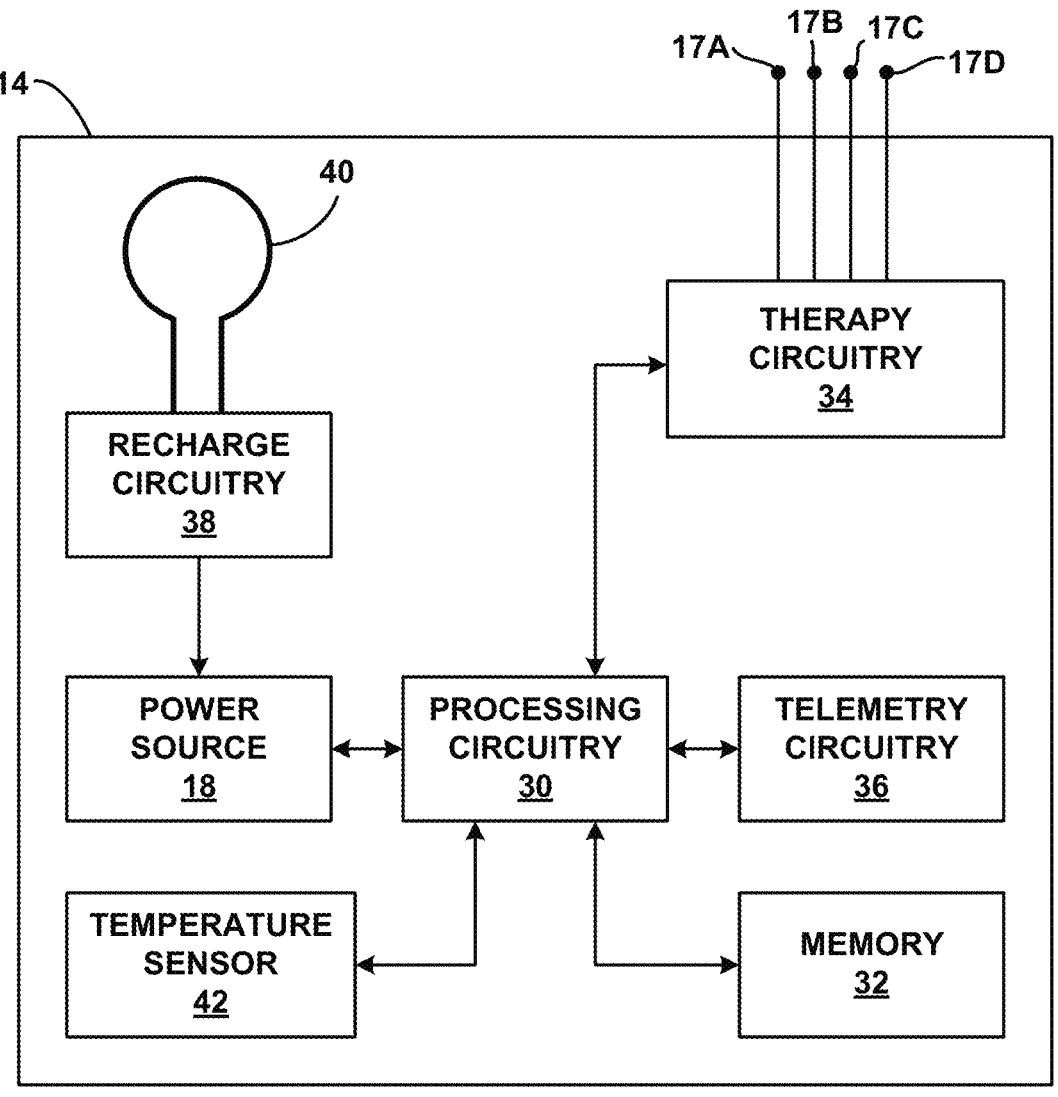
FIG. 2 is a block diagram of the example IMD of FIG. 1.

FIG. 2 is a block diagram illustrating example components of IMD 14. In the example of FIG. 2, IMD 14 includes temperature sensor 42, coil 40, processing circuitry 30, therapy circuitry 34, recharge circuitry 38, memory 32, telemetry circuitry 36, and rechargeable power source 18. In other examples, IMD 14 may include a greater or a fewer number of components. For example, in some examples, IMD 14 may not include temperature sensor 42.

In general, IMD 14 may comprise any suitable arrangement of hardware, alone or in combination with software and/or firmware, to perform the various techniques described herein attributed to IMD 14 and processing circuitry 30. In various examples, IMD 14 may include one or more processors 30, such as one or more microprocessors, digital signal processors (DSPs), application specific integrated circuits (ASICs), field programmable gate arrays (FPGAs), or any other equivalent integrated or discrete logic circuitry, as well as any combinations of such components. IMD 14 also, in various examples, may include a memory 32, such as random access memory (RAM), read only memory (ROM), programmable read only memory (PROM), erasable programmable read only memory (EPROM), electronically erasable programmable read only memory (EEPROM), flash memory, comprising executable instructions for causing the one or more processors to perform the actions attributed to them. Moreover, although processing circuitry 30, therapy circuitry 34, recharge circuitry 38, and telemetry circuitry 36 are described as separate circuitries, in some examples, processing circuitry 30, therapy circuitry 34, recharge circuitry 38, and telemetry circuitry 36 are functionally integrated. In some examples, processing circuitry 30, therapy circuitry 34, recharge circuitry 38, and telemetry circuitry 36 correspond to individual hardware units, such as ASICs, DSPs, FPGAs, or other hardware units.

Memory 32 may store therapy programs or other instructions that specify therapy parameter values for the therapy provided by therapy circuitry 34 and IMD 14. In some examples, memory 32 may also store temperature data from temperature sensor 42, instructions for recharging rechargeable power source 18, thresholds, instructions for communication between IMD 14 and charging device 22, or any other instructions required to perform tasks attributed to IMD 14. Memory 32 may be configured to store instructions for communication with and/or controlling one or more temperature sensors 42. As described herein, the temperature sensor 42 may be an IR sensor, a phosphor temperature sensor, or any other non-contact sensor or sensor (whether or not contact) that senses temperature by means other than thermal coupling.

Generally, therapy circuitry 34 may generate and deliver electrical stimulation under the control of processing circuitry 30. In some examples, processing circuitry 30 controls therapy circuitry 34 by accessing memory 32 to selectively access and load at least one of the stimulation programs to therapy circuitry 34. For example, in operation, processing circuitry 30 may access memory 32 to load one of the stimulation programs to therapy circuitry 34. In such examples, relevant stimulation parameters may include a voltage amplitude, a current amplitude, a pulse rate, a pulse width, a duty cycle, or the combination of electrodes 17A, 17B, 17C, and 17D that therapy circuitry 34 uses to deliver the electrical stimulation signal. Therapy circuitry 34 may be configured to generate and deliver electrical stimulation therapy via one or more of electrodes 17A, 17B, 17C, and 17D of lead 16. Alternatively, or additionally, therapy circuitry 34 may be configured to provide different therapy to patient 12. For example, therapy circuitry 34 may be configured to deliver drug delivery therapy via a catheter. These and other therapies may be provided by IMD 14.

IMD also includes components to receive power from charging device 22 to recharge rechargeable power source 18 when rechargeable power source 18 has been at least partially depleted. As shown in FIG. 2, IMD 14 includes secondary coil 40 and recharge circuitry 38 coupled to rechargeable power source 18. Recharge circuitry 38 may be configured to charge rechargeable power source 18 with the selected power level determined by either processing circuitry 30 or charging device 22. Recharge circuitry 38 may include any of a variety of charging and/or control circuitry configured to process or convert current induced in coil 40 into charging current to charge power source 18. Although processing circuitry 30 may provide some commands to recharge circuitry 38, in some examples, processing circuitry 30 may not need to control any aspect of recharging.

Secondary coil 40 may include a coil of wire or other device capable of inductive coupling with a primary coil disposed external to patient 12. Although secondary coil 40 is illustrated as a simple loop of in FIG. 2, secondary coil 40 may include multiple turns of conductive wire. Secondary coil 40 may include a winding of wire configured such that an electrical current can be induced within secondary coil 40 from a magnetic field. The induced electrical current may then be used to recharge rechargeable power source 18. In this manner, the electrical current may be induced in secondary coil 40 associated with rechargeable power source 18. The induction may be caused by electrical current generated in the primary coil of charging device 22, where the level of the current may be based on the selected power level. The coupling between secondary coil 40 and the primary coil of charging device 22 may be dependent upon the alignment of the two coils. Generally, the coupling efficiency increases when the two coils share a common axis and are in close proximity to each other. Charging device 22 and/or IMD 14 may provide one or more audible tones or visual indications of the alignment.

Although inductive coupling is generally described as the method for recharging rechargeable power source 18, other wireless energy transfer techniques may alternatively be used. Any of these techniques may generate heat in IMD 14 such that the charging process can be controlled by matching the sensed temperature to one or more thresholds, modeling tissue temperatures based on the sensed temperature, or using a calculated cumulative thermal dose as feedback.

Recharge circuitry 38 may include one or more circuits that process, filter, convert and/or transform the electrical signal induced in secondary coil to an electrical signal capable of recharging rechargeable power source 18. For example, in alternating current induction, recharge circuitry

38 may include a half-wave rectifier circuit and/or a full-wave rectifier circuit configured to convert alternating current from the induction to a direct current for rechargeable power source 18. The full-wave rectifier circuit may be more efficient at converting the induced energy for rechargeable power source 18. However, a half-wave rectifier circuit may be used to store energy in rechargeable power source 18 at a slower rate. In some examples, recharge circuitry 38 may include both a full-wave rectifier circuit and a half-wave rectifier circuit such that recharge circuitry 38 may switch between each circuit to control the charging rate of rechargeable power source 18 and temperature of IMD 14.

Rechargeable power source 18 may include one or more capacitors, batteries, and/or other energy storage devices. Rechargeable power source 18 may deliver operating power to the components of IMD 14. In some examples, rechargeable power source 18 may include a power generation circuit to produce the operating power. Rechargeable power source 18 may be configured to operate through hundreds or thousands of discharge and recharge cycles. Rechargeable power source 18 may also be configured to provide operational power to IMD 14 during the recharge process. In some examples, rechargeable power source 18 may be constructed with materials to reduce the amount of heat generated during charging. In other examples, IMD 14 may be constructed of materials that may help dissipate generated heat at rechargeable power source 18, recharge circuitry 38, and/or secondary coil 40 over a larger surface area of the housing of IMD 14.

Although rechargeable power source 18, recharge circuitry 38, and secondary coil 40 are shown as contained within the housing of IMD 14, in alternative implementations, at least one of these components may be disposed outside of the housing. For example, in some implementations, secondary coil 40 may be disposed outside of the housing of IMD 14 to facilitate better coupling between secondary coil 40 and the primary coil of charging device 22. These different configurations of IMD 14 components may allow IMD 14 to be implanted in different anatomical spaces or facilitate better inductive coupling alignment between the primary and secondary coils.

IMD 14 may also include temperature sensor 42. Temperature sensor 42 may include one or more temperature sensors configured to measure the temperature of respective portions of IMD 14. As described herein, a temperature sensor is thermally coupled to, and/or may be directly attached to, the portion of the device from which temperature is to be measured. In one instance, the temperature sensor is directly coupled with a portion of the interior of the IMD housing, such as an interior surface of the housing.

Temperature sensor 42 may be oriented to measure the temperature of a component, surface or structure (e.g., the housing) of IMD 14. Temperature sensor 42 may be disposed internal of the housing of IMD 14. Processing circuitry 30, or charging device 22, may use this temperature measurement as the tissue temperature feedback to control the power levels or charge times (e.g., cycle times) used during the charging session. Although a single temperature sensor may be adequate, multiple temperature sensors may provide more specific temperature readings of separate components or different areas of the housing. Although processing circuitry 30 may continually measure temperature using temperature sensor 42, processing circuitry 30 may conserve energy by only measuring temperature during recharge sessions. Further, temperature may be sampled at a rate necessary to effectively control the charging session, but the sampling rate may be reduced to conserve power as appropriate.

Processing circuitry 30 may also control the exchange of information with charging device 22 and/or an external programmer using telemetry circuitry 36. Telemetry circuitry 36 may be configured for wireless communication using radio frequency protocols or inductive communication protocols. Telemetry circuitry 36 may include one or more antennas configured to communicate with charging device 22, for example. Processing circuitry 30 may transmit operational information and receive therapy programs or therapy parameter adjustments via telemetry circuitry 36. Also, in some examples, IMD 14 may communicate with other implanted devices, such as stimulators, control devices, or sensors, via telemetry circuitry 36. In addition, telemetry circuitry 36 may be configured to transmit the measured tissue temperatures from temperature sensor 42, for example.

In other examples, processing circuitry 30 may transmit additional information to charging device 22 related to the operation of rechargeable power source 18. For example, processing circuitry 30 may use telemetry circuitry 36 to transmit indications that rechargeable power source 18 is completely charged, rechargeable power source 18 is fully discharged, or any other charge status of rechargeable power source 18. Processing circuitry 30 may also transmit information to charging device 22 that indicates any problems or errors with rechargeable power source 18 that may prevent rechargeable power source 18 from providing operational power to the components of IMD 14.

Figure 3:
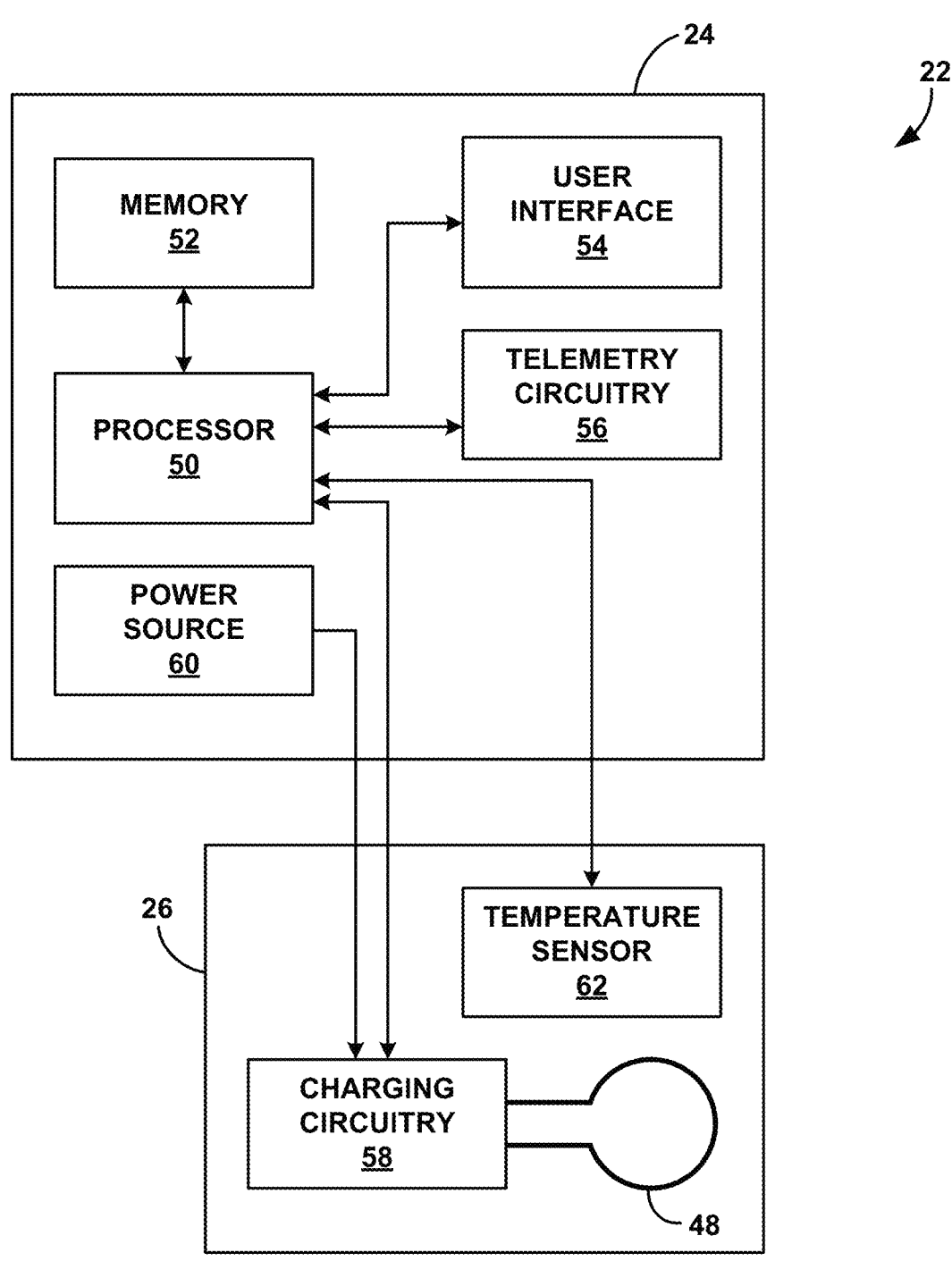
FIG. 3 is a block diagram of the example external charging device of FIG. 1.

FIG. 3 is a block diagram of the example external charging device 22. While charging device 22 may generally be described as a hand-held device, charging device 22 may be a larger portable device or a more stationary device. In addition, in other examples, charging device 22 may be included as part of an external programmer or include functionality of an external programmer. In addition, charging device 22 may be configured to communicate with an external programmer. As shown in FIG. 3, charging device 22 includes two separate components. Housing 24 encloses components such as a processor 50, memory 52, user interface 54, telemetry circuitry 56, and power source 60. Charging head 26 may include power circuitry 58, temperature sensor 62, and coil 48. A different partitioning of components is also possible, such as including one or more of the foregoing components within a circuitry carried by the cord of charging device 22.

A separate charging head 26 may facilitate optimal positioning of coil 48 over coil 40 of IMD 14. However, charging circuitry 58 and/or coil 48 may be integrated within housing 24 in other examples. Memory 52 may store instructions that, when executed by processor 50, cause processor 50 and external charging device 22 to provide the functionality ascribed to external charging device 22 throughout this disclosure.

External charging device 22 may also include one or more temperature sensors 62, similar to temperature sensor 42 of FIG. 2. Temperature sensor 62 may be disposed within charging head 26 and/or housing 24. For example, charging head 26 may include one or more temperature sensors positioned and configured to sense the temperature of coil 48 and/or a surface of the housing of charging head 26. In some examples, charging device 22 may not include temperature sensor 62.

In general, charging device 22 comprises any suitable arrangement of hardware, alone or in combination with software and/or firmware, to perform the techniques attributed to charging device 22, and processor 50, user interface 54, telemetry circuitry 56, and charging circuitry 58 of charging device 22. In various examples, charging device 22 may include one or more processors, such as one or more microprocessors, DSPs, ASICs, FPGAs, or any other equivalent integrated or discrete logic circuitry, as well as any combinations of such components. Charging device 22 also, in various examples, may include a memory 52, such as RAM, ROM, PROM, EPROM, EEPROM, flash memory, a hard disk, a CD-ROM, comprising executable instructions for causing the one or more processors to perform the actions attributed to them. Moreover, although processor 50 and telemetry circuitry 56 are described as separate circuitries, in some examples, processor 50 and telemetry circuitry 56 are functionally integrated. In some examples, processor 50 and telemetry circuitry 56 and charging circuitry 58 correspond to individual hardware units, such as ASICs, DSPs, FPGAs, or other hardware units.

Memory 52 may store instructions that, when executed by processor 50, cause processor 50 and charging device 22 to provide the functionality ascribed to charging device 22 throughout this disclosure. For example, memory 52 may include instructions that cause processor 50 to control the power level used to charge IMD 14 in response to the sensed temperatures, communicate with IMD 14, or instructions for any other functionality. In addition, memory 52 may include a record of selected power levels, sensed temperatures, or any other data related to charging rechargeable power source 18. Processor 50 may, when requested, transmit any of this stored data in memory 52 to another computing device for review or further processing.

User interface 54 may include a button or keypad, lights, a speaker for voice commands, a display, such as a liquid crystal (LCD), light-emitting diode (LED), or cathode ray tube (CRT). In some examples the display may be a touch screen. As discussed in this disclosure, processor 50 may present and receive information relating to the charging of rechargeable power source 18 via user interface 54. For example, user interface 54 may indicate when charging is occurring, quality of the alignment between coils 40 and 48, the selected power level, current charge level of rechargeable power source 18, duration of the current recharge session, anticipated remaining time of the charging session, sensed temperatures, instructions for changing a phase change material cartridge of charging head 26, or any other information. Processor 50 may receive some of the information displayed on user interface 54 from IMD 14 in some examples.

User interface 54 may also receive user input via user interface 54. The input may be, for example, in the form of pressing a button on a keypad or selecting an icon from a touch screen. The input may request starting or stopping a recharge session, a desired level of charging, or one or more statistics related to charging rechargeable power source 18 (e.g., the cumulative thermal dose). In this manner, user interface 54 may allow the user to view information related to the charging of rechargeable power source 18 and/or receive charging commands.

Charging device 22 also includes components to transmit power to recharge rechargeable power source 18 associated with IMD 14. As shown in FIG. 3, charging device 22 includes primary coil 48 and charging circuitry 58 coupled to power source 60. Charging circuitry 58 may be configured to generate an electrical current in primary coil 48 from voltage stored in power source 60. Although primary coil 48 is illustrated as a simple loop in FIG. 3, primary coil 48 may include multiple turns of wire. Charging circuitry 58 may generate the electrical current according to a power level selected by processor 50 based on the sensed temperature or temperatures received from IMD 14 or a temperature sensor within charging device 22. As described herein, processor 50 may select a high power level, low power level, or a variety of different power levels to control the rate of recharge in rechargeable power source 18 and the temperature of IMD 14. In some examples, processor 50 may control charging circuitry 58 based on a power level selected by processing circuitry 30 of IMD 14. The sensed temperature used as feedback for control of the recharge power level may be from a temperature sensed by a temperature sensor within IMD 14 and/or charging device 22. Although processor 50 may control the power level used for charging rechargeable power source 18, charging circuitry 58 may include one or more processors configured to partially or fully control the power level based on the sensed temperatures.

Primary coil 48 may include a coil of wire, e.g., having multiple turns, or other device capable of inductive coupling with a secondary coil 40 disposed within patient 12. Primary coil 48 may include a winding of wire configured such that an electrical current generated within primary coil 48 can produce a magnetic field configured to induce an electrical current within secondary coil 40. The induced electrical current may then be used to recharge rechargeable power source 18. In this manner, the electrical current may be induced in secondary coil 40 associated with rechargeable power source 18. The coupling efficiency between secondary coil 40 and primary coil 48 of charging device 22 may be dependent upon the alignment of the two coils. Generally, the coupling efficiency increases when the two coils share a common axis and are in close proximity to each other. User interface 54 of charging device 22 may provide one or more audible tones or visual indications of the alignment.

Charging circuitry 58 may include one or more circuits that generate an electrical signal, and an electrical current, within primary coil 48. Charging circuitry 58 may generate an alternating current of specified amplitude and frequency in some examples. In other examples, charging circuitry 58 may generate a direct current. In any case, charging circuitry 58 may be capable of generating electrical signals, and subsequent magnetic fields, to transmit various levels of power to IMD 14. In this manner charging circuitry 58 may be configured to charge rechargeable power source 18 of IMD 14 with the selected power level.

The power level that charging circuitry 58 selects for charging may be used to vary one or more parameters of the electrical signal generated for coil 48. For example, the selected power level may specify wattage, electrical current of primary coil 48 or secondary coil 40, current amplitude, voltage amplitude, pulse rate, pulse width, a cycling rate that determines when the primary coil is driven, or any other parameter that may be used to modulate the power transmitted from coil 48. In this manner, each power level may include a specific parameter set that specifies the signal for each power level. Changing from one power level to another power level (e.g., a high power level to a lower power level) may include adjusting one or more parameters. For instance, at a high power level, the primary coil may be substantially continuously driven, whereas at a lower power level, the primary coil may be intermittently driven such that periodically the coil is not driven for a predetermined time to control heat dissipation. The parameters of each power level may be selected based on hardware characteristics of charging device 22 and/or IMD 14.

Power source 60 may deliver operating power to the components of charging device 22. Power source 60 may also deliver the operating power to drive primary coil 48 during the charging process. Power source 60 may include a battery and a power generation circuit to produce the operating power. In some examples, a battery of power source 60 may be rechargeable to allow extended portable operation. In other examples, power source 60 may draw power from a wired voltage source such as a consumer or commercial power outlet.

Charging device 22 may include one or more temperature sensor 62 for sensing the temperature of a portion of the device. For example, temperature sensor 62 may be disposed within charging head 26 and oriented to sense the temperature of the housing of charging head 26. In another example, temperature sensor 62 may be disposed within charging head 26 and oriented to sense the temperature of charging circuitry 58 and/or coil 48. In other examples, charging device 22 may include multiple temperature sensors 62 each oriented to any of these portions of device to manage the temperature of the device during charging sessions.

Telemetry circuitry 56 supports wireless communication between IMD 14 and charging device 22 under the control of processor 50. Telemetry circuitry 56 may also be configured to communicate with another computing device via wireless communication techniques, or direct communication through a wired connection. In some examples, telemetry circuitry 56 may be substantially similar to telemetry circuitry 36 of IMD 14 described herein, providing wireless communication via an RF or proximal inductive medium. In some examples, telemetry circuitry 56 may include an antenna, which may take on a variety of forms, such as an internal or external antenna. Although telemetry circuitries 56 and 36 may each include dedicated antennae, telemetry circuitries 56 and 36 may instead, or additionally, be configured to utilize inductive coupling from coils 40 and 48 to transfer data.

Examples of local wireless communication techniques that may be employed to facilitate communication between charging device 22 and IMD 14 include radio frequency and/or inductive communication according to any of a variety of standard or proprietary telemetry protocols, or according to other telemetry protocols such as the IEEE 802.11x or Bluetooth specification sets. In this manner, other external devices may be capable of communicating with charging device 22 without needing to establish a secure wireless connection. As described herein, telemetry circuitry 56 may be configured to receive a signal or data representative of a measured tissue temperature from IMD 14. The tissue temperature may be indirectly measured by measuring the temperature of the internal surface of the IMD housing adjacent to rechargeable power source 18. In some examples, multiple temperature readings by IMD 14 may be averaged or otherwise used to produce a single temperature value that is transmitted to charging device 22. The sensed temperature may be sampled and/or transmitted by IMD 14 (and received by charging device 22) at different rates, e.g., on the order of microseconds, milliseconds, seconds, minutes, or even hours. Processor 50 may then use the received temperature to control charging of rechargeable power source 18 (e.g., control the charging level used to recharge power source 18).

FIGS. 4A-4E are conceptual cross-sectional views of example temperature sensors 150 disposed within respective example IMDs 100. Any of IMDs 100A-100E are examples of IMD 14 of FIGS. 1 and 2. The IMDs described herein are generally shown with rectangular cross-sections. However, temperature sensors may be disposed within IMDs or any other devices of any shapes, dimensions, or sizes.

Figure 4A:
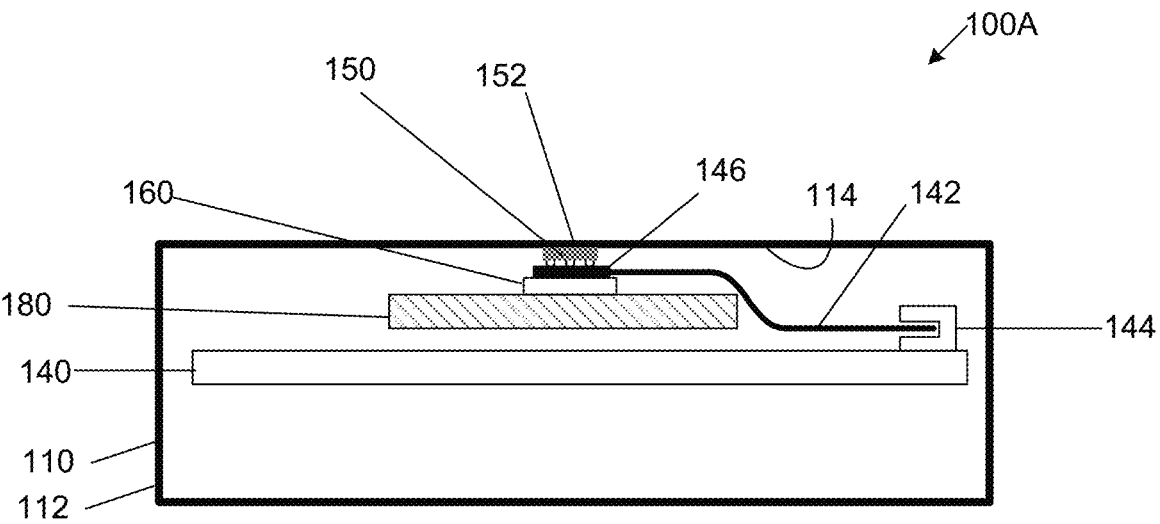
FIG. 4A is a cross-sectional view of an example IMD that includes a temperature sensor disposed within the IMD.

As shown in FIG. 4A, IMD 100A includes housing 110 that encloses hybrid board 140, electronics, temperature sensor 150, compliant material 160 and support 180. Electronics may include various components such as a processor and memory and associated circuitry. A secondary coil and rechargeable power source may also be disposed within housing 110. The hybrid board 140 may be electrically coupled with the temperature sensor 150 with a flexible circuit 142, and may provide a flexible and electrical connection between the hybrid board 140 and the temperature sensor 150. In one or more examples, a connector 144 may be disposed on and/or electrically coupled with the hybrid board 140 and may be coupled with the flexible circuit 142, and may facilitate the electrical connection between the flexible circuit 142 and the hybrid board 140. IMD 100 may include additional components in other examples, or in other areas of IMD 100 not shown in the particular cross-section of FIG. 4A.

Figure 4B:
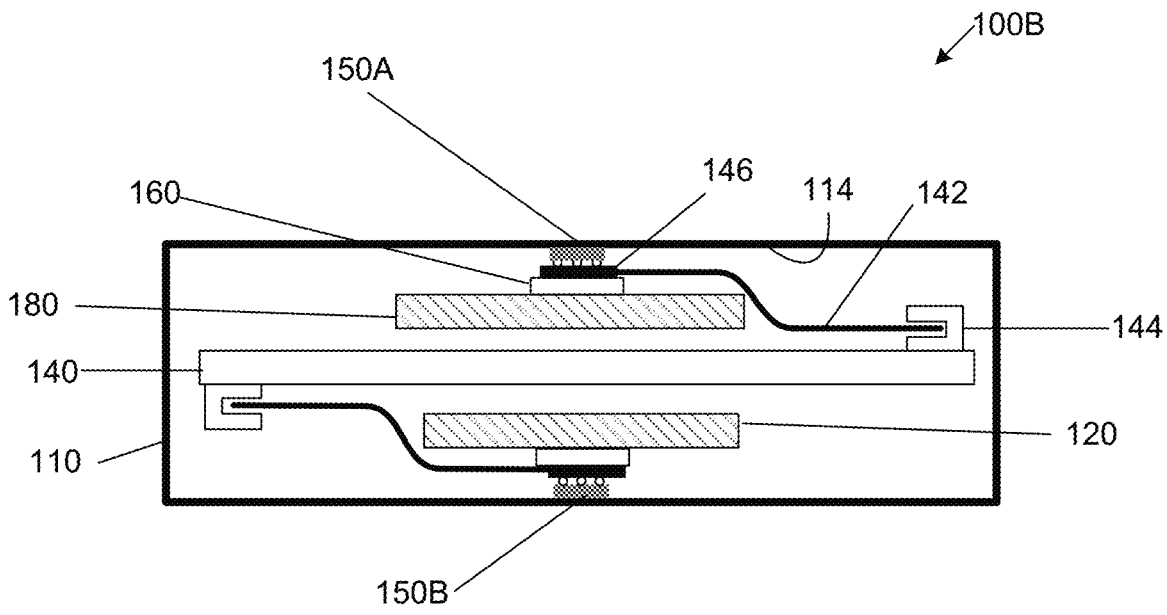
FIG. 4B is a cross-sectional view of an example IMD that includes a temperature sensors disposed within the IMD.

The housing 110 includes an exterior surface 112 and an interior surface 114, and/or in some examples constructed of a titanium alloy. In some examples, the housing 110 is a titanium shield configured to protect components within the housing 110 such as a temperature sensor. In one or more examples, the housing 110 may include a cup shaped housing 126 and lid 128, as shown in the IMD 100D of FIG. 4D. The components discussed above may be assembled and set within the cup shaped housing 126. In some examples, a method of assembly may include welding the lid 128 to the cup shaped housing 126, for example, at weld 118 after the components are set therein. In one or more examples, as shown in FIG. 4E, IMD 100E includes housing 110 which may include a sleeve 120 that connects with header 124, where the sleeve 120 may be slid over the components therein and may be welded to the header 124 at weld 118.

Figure 5:
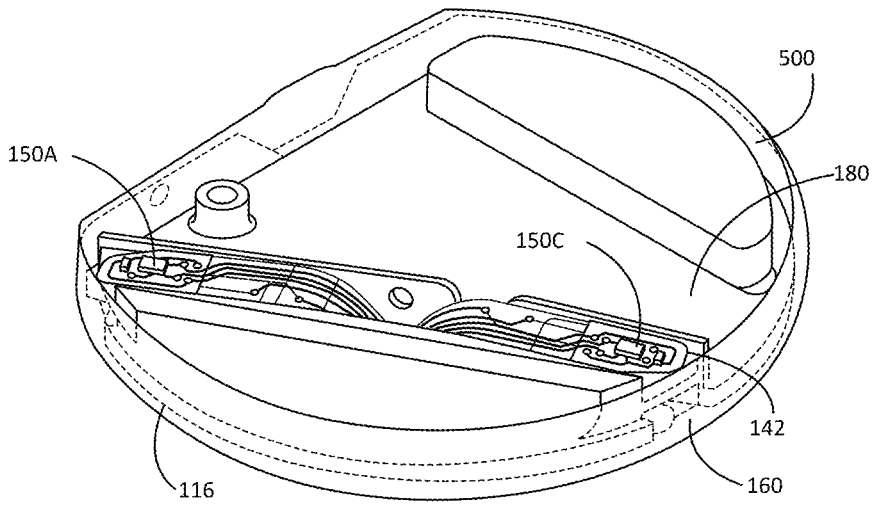
FIG. 5 is a conceptual diagram illustrating an example IMD that includes temperature sensor(s) disposed within the IMD.
Figure 6:
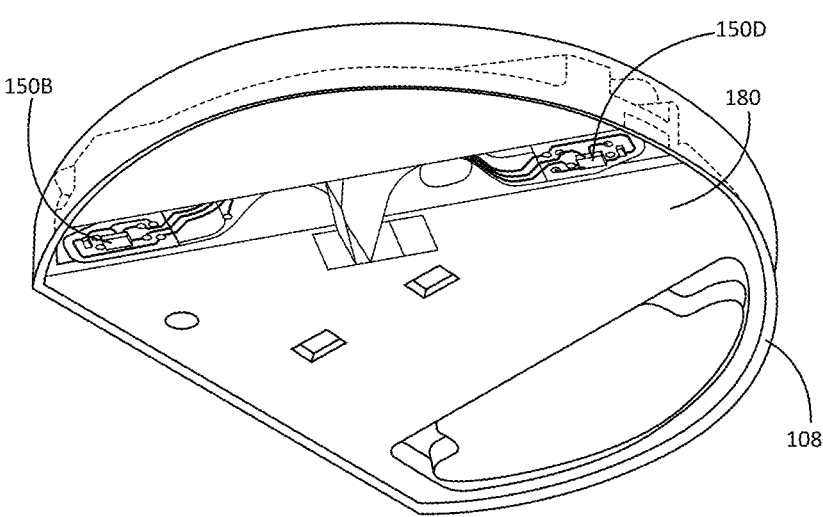
FIG. 6 is a conceptual diagram illustrating an example IMD that includes temperature sensor(s) disposed within the IMD.
Figure 7:
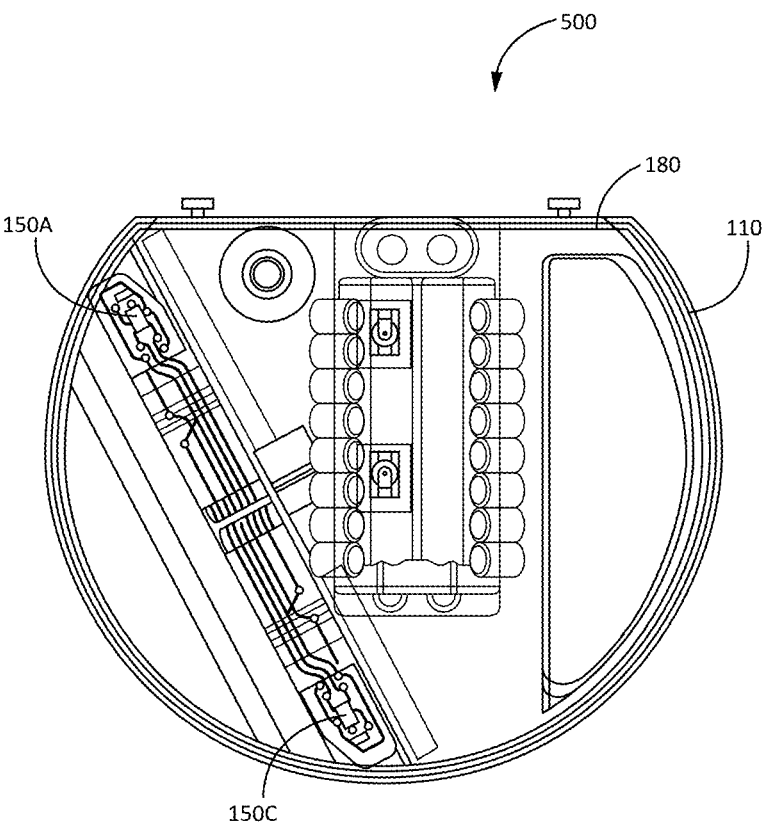
FIG. 7 is a conceptual diagram illustrating an example IMD that includes temperature sensor(s) disposed within the IMD.
Figure 8:
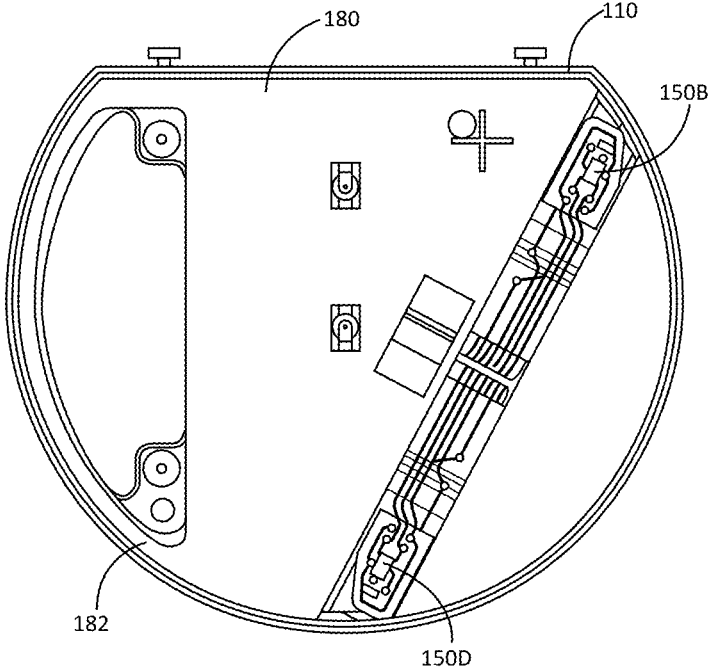
FIG. 8 is a conceptual diagram illustrating an example support configured to be disposed within an IMD.

FIGS. 5-8 illustrate a support 180 in greater detail, where FIGS. 5-6 show an IMD 500 with a translucent housing, FIG. 7 shows a top view of an IMD, and FIG. 8 shows a bottom view of the IMD with the support 180. In one or more examples, at least one support 180 may be disposed within the housing 110, and/or in one or more examples may be mechanically coupled with the housing and/or other components within the housing 110, for example to the interior surface 114 of the housing 110. In one or more examples, the at least one support 180 may extend from or is in contact with one or more locations of the interior surface 114 of the housing 110. In one or more examples, the at least one support 180 may be in contact with two or more interior surfaces 114 of the housing 110. In one or more examples, the at least one support 180 may be in contact with two or more interior surfaces 114 of the housing 110, such as opposing side surfaces and/or top/bottom surfaces. In one or more examples, the at least one support 180 may have a clearance fit with the housing 110. In one or more examples, the at least one support 180 may have a friction fit with the housing 110. In some examples, at least one support 180 may include structure such as tabs, projections, and/or recesses to couple components therewith. For example, support 180 may include tabs in which the hybrid board 140 may be snapped. In some examples, support 180 may be formed together with housing 110 or attached using material coupling techniques such as welding or soldering.

In one or more examples, the at least one support 180, or a portion thereof, may include a planar ledge configured to accommodate devices, including electronics or sensors, to be disposed thereon or therein. In one or more examples, the at least one support 180, or a portion thereof, may include a curved cup-like structure configured to accommodate devices, including electronics or sensors, to be disposed thereon or therein.

In some examples, the at least one support may be a rigid support, for example as rigid as housing 110. In one or more examples, at least one support 180 may be a rigid support, for example, lacking flexibility or unable to bed or be forced out of shape. In one or more examples, at least one support may be formed of machined plastic and/or metal.

Figure 9:
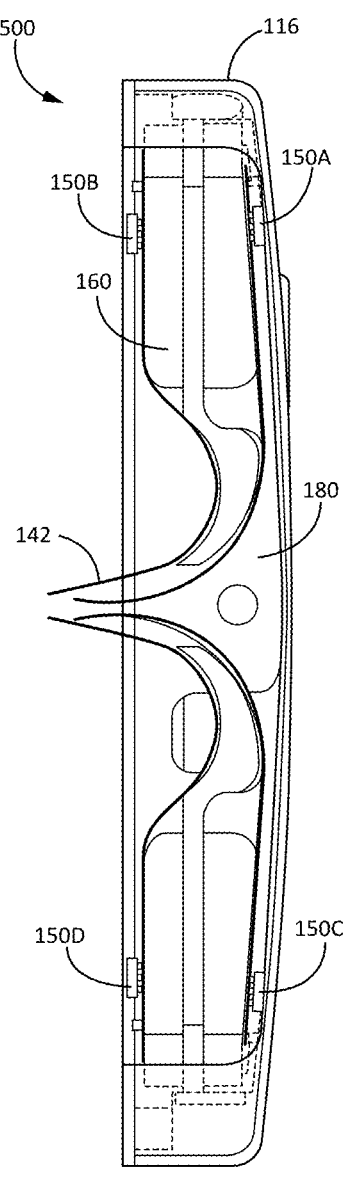
FIG. 9 is a cross-sectional view of an example IMD with temperature sensor(s) disposed within an IMD.

In one or more examples, the housing 110 includes one or more curved portions 116. For example, an upper edge of the housing may have curved edges as shown in FIG. 9. In one or more examples, an upper and lower edge of the housing 110 may have curved edges. In one or more examples, the support 180 may include a curved profile 182 as shown in FIG. 8, where the support curved profile 182 may be substantially similar to a curved side wall 108 (FIG. 6) of the housing 110 such that the support 180 is adjacent to a curved side interior portion of the housing 110, as shown in FIG. 5.

The IMD 100 includes one or more temperature sensor(s) 150. In some examples, the temperature sensor 150 may be a high-precision digital temperature sensor and/or having low power consumption. In one or more examples, the temperature sensor 150 may include multiple sensors, as shown in FIGS. 4B, 5-7, and 9. For example, the temperature sensor 150 may be a first sensor and the IMD 100 includes one or more additional temperature sensors disposed at multiple locations within the housing 110 and thermally coupled to respective portions of the interior surface 114 of the housing 110. In one or more examples, the temperature sensors 150A, 150B may be positioned to sense temperature on opposing sides of the housing 110, as shown in FIG. 4B. In some examples, at least four sensors may be disposed in the IMD 500, as shown in FIG. 9 In one or more examples, two sensors 150A, 150C may be disposed near a top portion of a housing, and/or two sensors 150B, 150D may be disposed near a bottom portion of the housing, for example as shown in FIGS. 5, 6, and 9. In some examples, sensing the temperature on opposing sides of IMD500 may be beneficial if IMD 500 becomes flipped within the tissue pocket containing IMD500 with the patient.

The temperature sensor 150 may be disposed within the housing 110, and the temperature sensor 150 may be thermally coupled to the interior surface 114 of the housing 110. In one or more examples, the temperature sensor 150 may be physically coupled to the housing 110 and/or directly coupled to the housing 110. In one or more examples, the temperature sensor 150 includes a sensor surface 152 that may be thermally coupled to the interior surface 114 of the housing 110. The temperature sensor may be configured to sense a temperature of a portion of the housing, for example the sensor surface 152 may be operable to sense a temperature. In one or more examples, the sensor surface 152 may be in direct contact with the interior surface 114 of the housing 110.

Figure 4C:
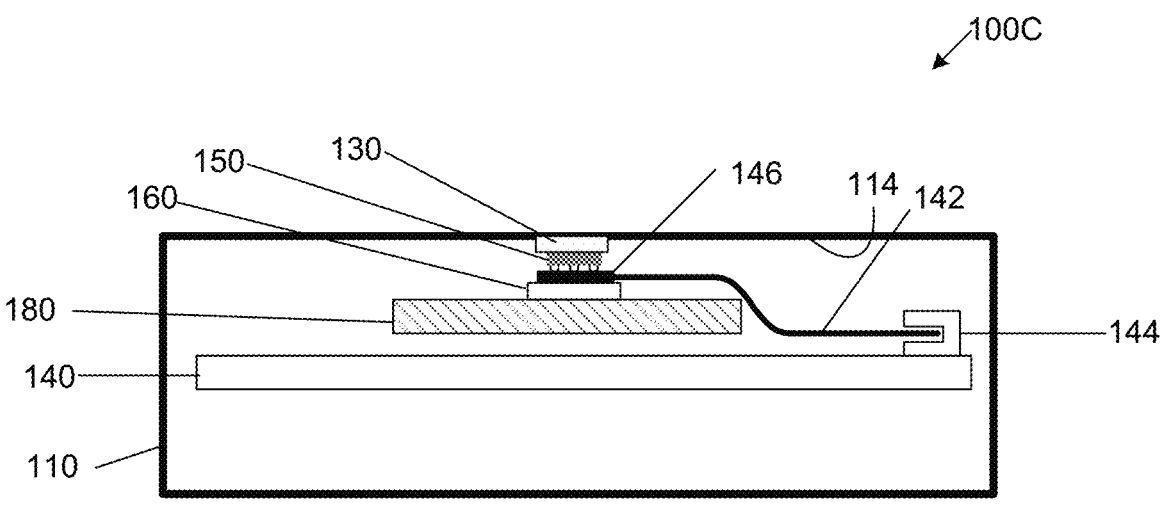
FIG. 4C is a cross-sectional view of an example IMD that includes a temperature sensor disposed within the IMD.

Referring to FIG. 4C, an exemplary IMD 100C is shown with a temperature sensor 150 disposed therein. In addition to temperature sensor 150, thermally conductive material 130 may be disposed within housing 110 and between housing 110 and temperature sensor 150 to transfer energy from the housing 110 to temperature sensor 150. In some examples, conductive material 130 (or another energy transfer structure) may transfer the energy from the desired housing surface to be sensed to temperature sensor 150. In the example of FIG. 4C, thermally conductive material 130 may be configured to be thermally coupled to the interior surface 114 of housing 110.

Figure 4D:
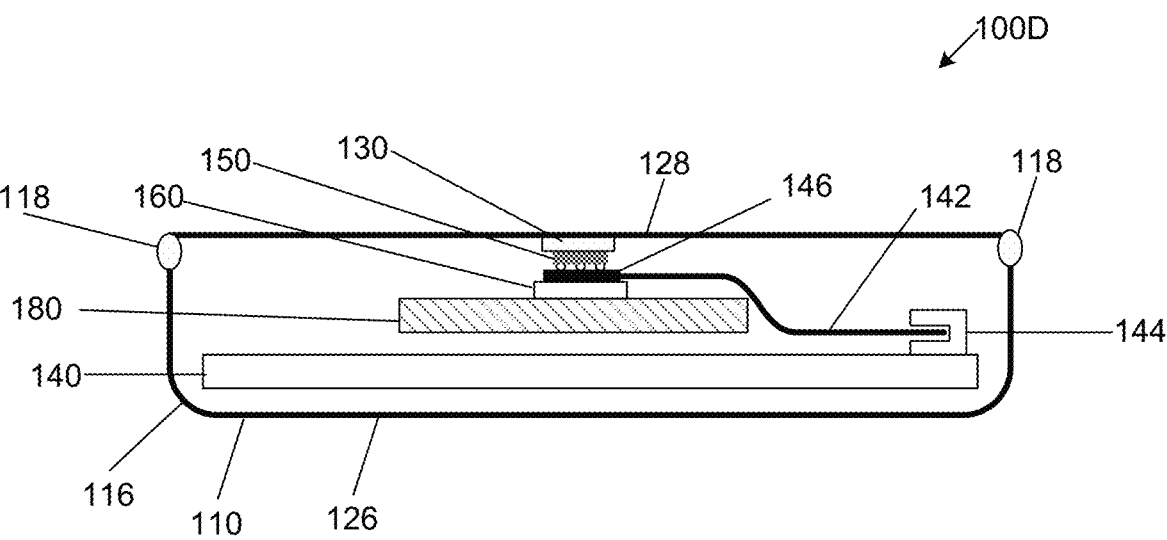
FIG. 4D is a cross-sectional view of an example IMD that includes a temperature sensor disposed within the IMD.
Figure 4E:
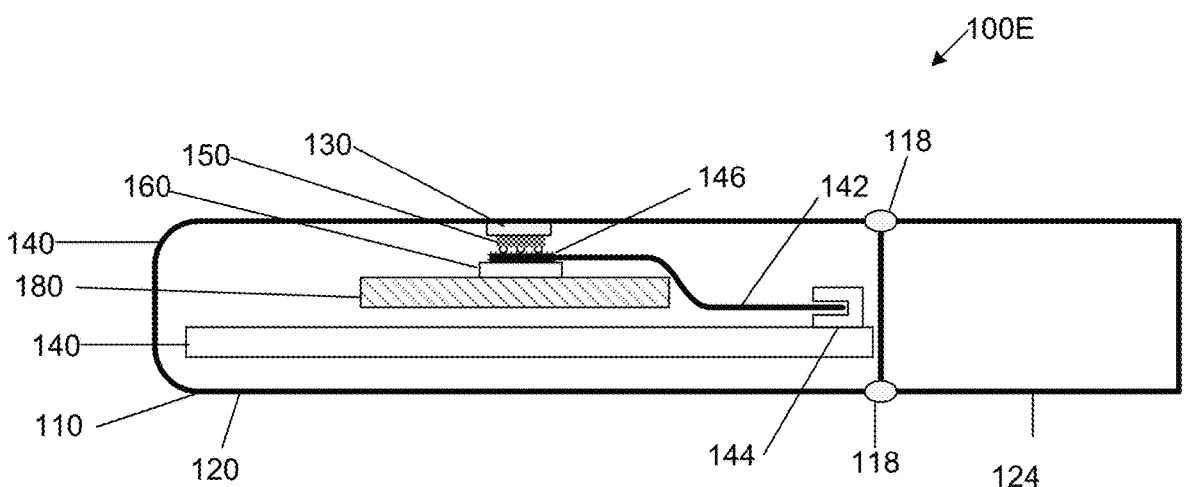
FIG. 4E is a cross-sectional view of an example IMD that includes a temperature sensor disposed within the IMD.

Although only one thermally conductive material 130 may be provided, IMD 100C may include two or more components of thermally conductive material to transfer energy from multiple portions within IMD, as shown in FIG. 4D. Examples of thermally conductive material may include a thermal pad such as a thermally conductive pad. The thermally conductive material 130 may be constructed of a solid structure, hollow structure, gel, paste, or any other configuration in which the thermally conductive material 130 conducts heat energy from the target surface (e.g., interior surface 114) to temperature sensor 150.

Thermally conductive material 130 may be configured within housing 110 to physically contact the interior surface 114 of housing 110. In some examples, thermally conductive material 130 may be constructed such that a free end of thermally conductive material 130 may be biased against curved portion 116 of housing 110 when housing 110 may be hermetically sealed around the interior components of IMD 100. In other words, closing housing 110 may cause curved portion to contact thermally conductive material 130 such that the structural stiffness of thermally conductive material 130 retains physical contact between thermally conductive material 130 and curved portion 134 and a surface of the sensor 150. In one or more examples, thermally conductive material may be configured to conform to the curved inner portion of the housing 110.

In one or more examples as shown in FIGS. 4A-4E, at least one physically compliant material 160 may be disposed between the at least one support 180 and the temperature sensor 150. In one or more examples, the at least one physically compliant material 160 may be configured to provide a physical bias against the temperature sensor and towards the interior surface of the housing. In one or more examples, the physically compliant material 160 may be configured to provide the physical bias to the temperature sensor 150 to maintain contact between the interior surface 114 of the housing 110 The at least one physically compliant material 160 includes an elastomer in one or more examples. Physically compliant material 160 may be solid, viscoelastic solid, gel, paste, or any other material configured to provide the physical bias. The physical bias may be generated by a shape of compliant material 160 and/or material properties of compliant material 160. The compliant material 160 make take up tolerance of the various components within the housing. In some examples, the compliant material 160 may be electrically insulative material. In some examples, compliant material 160 may be formed of one or more of elastic pad, compression pad, foam, rubber, or a diaphragm of plastic and/or metal configured to flex. In one or more examples, a stiffener 146 may be disposed between the compliant material 160 and the sensor 150. The stiffener 146 may be provided under components that are electrically coupled, for example soldered, to the flexible circuit 142. The stiffener 146 may prevent mechanical fatigue on solder joints and circuit components.

Figure 10:
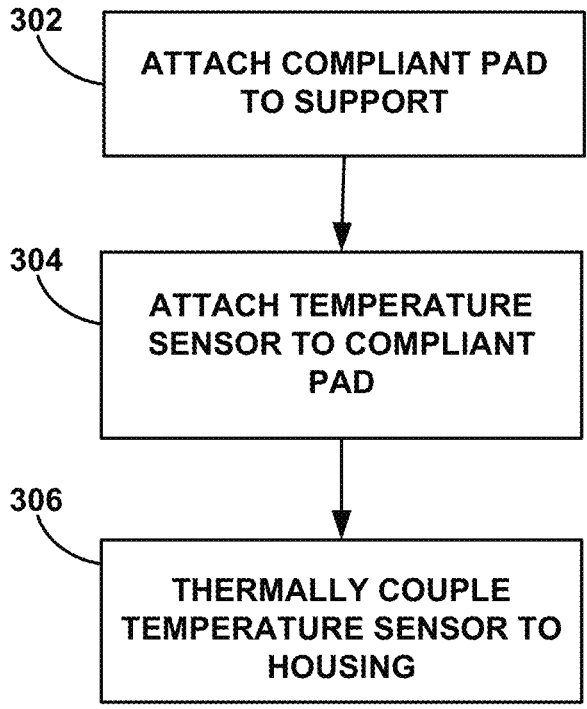
FIG. 10 is a flow diagram that illustrates an example technique for manufacturing an IMD.

FIG. 10 is a flow diagram that illustrates an example technique for manufacturing an IMD, such as any of IMDs 100A-100E. This technique may include disposing a temperature sensor within a housing, the housing comprising an exterior surface and an interior surface, the housing having at least one support in contact with the housing. In one or more examples, the at least one support may be coupled with an interior surface of the housing. In one or more examples, the method includes disposing multiple temperature sensors at multiple locations within the housing, and wherein each of the multiple temperature sensors are physically biased towards the interior surface of the housing with the physically compliant material. The method may further include disposing at least one physically compliant material between the at least one support and the temperature sensor, where the at least one physically compliant material may be configured to physically bias the temperature sensor towards the interior surface of the housing with the physically compliant material. In one or more examples, the method includes thermally coupling the temperature sensor to the housing, the temperature sensor configured to sense a temperature of a portion of the housing, the temperature sensor including a sensor surface.

In the example of FIG. 10, the manufacturing technique includes installing a hybrid board into the support, and may further include attaching a compliant pad to the support (302). The sensor may be attached to the support, and may be attached to the compliant pad (304). In some examples, the method includes thermally coupling the temperature sensor with a housing (306), for example the method includes disposing a sensing surface of the at least one temperature sensor directly adjacent to the interior surface of the housing wherein the sensing surface may be in direct contact with the interior surface of the housing. In one or more examples, the method may further include disposing a printed circuit board within the housing, and electrically coupling the temperature sensor with the hybrid board with a flexible circuit.

The method also includes thermally coupling the temperature sensor to the housing (304), where the temperature sensor may be configured to sense a temperature of a portion of the housing, and the temperature sensor may include a sensor surface. In one or more examples, the method may further include disposing thermally conductive material disposed between the sensor and the interior surface of the housing, and further optionally thermally connecting the thermally conductive material with the sensor surface and the interior surface of the housing.

Example 1: An implantable medical device includes a housing comprising an exterior surface and an interior surface; at least one support disposed within the housing; a temperature sensor comprising a sensor surface thermally coupled to the interior surface of the housing, wherein the temperature sensor is disposed within the housing and configured to sense a temperature of a portion of the housing; and at least one physically compliant material disposed between the at least one support and the temperature sensor, wherein the physically compliant material is configured to provide a physical bias against the temperature sensor and towards the interior surface of the housing.

Example 2: The implantable medical device of example 1, wherein the at least one physically compliant material is configured to provide the physical bias to the temperature sensor to maintain contact between the interior surface of the housing and the sensor surface of the temperature sensor.

Example 3: The implantable medical device of any of examples 1 and 2, wherein the at least one support contacts at least two opposing interior surfaces of the housing.

Example 4: The implantable medical device of any of examples 1 through 3, wherein the sensor surface is an operable sensing surface and the sensing surface is disposed directly in contact with the interior surface of the housing.

Example 5: The implantable medical device of any of examples 1 through 4, further includes a hybrid board disposed within the housing; and a flexible circuit electrically coupling the temperature sensor to the hybrid board.

Example 6: The implantable medical device of any of examples 1 through 5, wherein the at least one support is in contact with the interior surface of the housing.

Example 7: The implantable medical device of any of examples 1 through 6, wherein the at least one support is a rigid support.

Example 8: The implantable medical device of any of examples 1 through 7, wherein the physically compliant material is an elastic pad.

Example 9: The implantable medical device of any of examples 1 through 8, further comprising a thermally conductive material disposed between the sensor surface and the interior surface of the housing.

Example 10: The implantable medical device of example 9, wherein the housing comprises a curved inner portion, and wherein the thermally conductive material is configured to conform to the curved inner portion to couple the sensor surface and the interior surface of the housing.

Example 11: The implantable medical device of any of examples 1 through 10, wherein the temperature sensor is a first temperature sensor, and wherein the implantable medical device comprises one or more additional temperature sensors disposed at multiple locations within the housing and thermally coupled to respective portions of the interior surface of the housing.

Example 12: The implantable medical device of any of examples 1 through 11, wherein the housing is a titanium shield configured to protect the temperature sensor.

Example 13: The implantable medical device of any of examples 1 through 12, further comprising processing circuitry configured to receive a temperature signal from the temperature sensor and control at least one function of the implantable medical device based on the temperature signal.

Example 14: A method includes at least one physically compliant material at least one support where the at least one physically compliant material is configured to physically bias the temperature sensor towards the interior surface of the housing with the physically compliant material; and thermally coupling the temperature sensor to the housing, the temperature sensor configured to sense a temperature of a portion of the housing, the temperature sensor including a sensor surface.

Example 15: The method of example 14, further comprising disposing a sensing surface of the temperature sensor directly adjacent to the interior surface of the housing wherein the sensing surface is in direct contact with the interior surface of the housing.

Example 16: The method of any of examples 14 and 15, further comprising disposing a hybrid board within the housing, and electrically coupling the temperature sensor with the hybrid board with a flexible circuit.

Example 17: The method of any of examples 14 through 16, further comprising disposing thermally conductive material disposed between the temperature sensor and the interior surface of the housing.

Example 18: The method of example 17, further comprising thermally connecting the thermally conductive material with the sensor surface and the interior surface of the housing.

Example 19: The method of any of examples 14 through 18, further comprising disposing multiple temperature sensors at multiple locations within the housing, and wherein each of the multiple temperature sensors are physically biased towards the interior surface of the housing with the physically compliant material.

Example 20: An implantable medical device includes a housing comprising an exterior surface and an interior surface; at least one support disposed within the housing; a temperature sensor comprising a sensor surface thermally coupled to the interior surface of the housing, wherein the temperature sensor is disposed within the housing and configured to sense a temperature of a portion of the housing; at least one physically compliant material disposed between the at least one support and the temperature sensor, wherein the physically compliant material is configured to provide a physical bias against the temperature sensor and towards the interior surface of the housing.

According to the techniques and devices described herein, an IMD or external charging device may include one or more temperature sensors configured to sense the temperature of a portion of the device directly coupled or thermally coupled to the temperature sensor. These temperature sensors may be mounted on an interior surface of the IMD housing. In this manner, temperature sensors may obtain temperature information about one or more portions of the device while being thermally coupled to the interior surface of the IMD housing. The IMD and/or external charging device may then control charging of an implantable rechargeable power source using the sensed temperatures.

This disclosure is primarily directed to wireless transfer of energy between two coils (e.g., inductive coupling). However, one or more aspects of this disclosure may also be applicable to energy transfer involving a physical connection between a charging device and a rechargeable power supply. For example, aspects of this disclosure may be applicable to charging the power supply of an IMD by inserting a needle coupled to an external charging device through the skin and into a port of the IMD. Although physical connections for energy transfer may not introduce heat losses due to energy transfer between wireless coils, heat may still be generated and lost to the patient from components within the IMD (e.g., the battery being charged and circuits involved in the recharging of the power supply). In addition, the temperature sensors described herein may be used to monitor temperature for any application related to the operation, status, or condition of the device or device surroundings.

The disclosure also contemplates computer-readable storage media comprising instructions to cause a processor to perform any of the functions and techniques described herein. The computer-readable storage media may take the form of any volatile, non-volatile, magnetic, optical, or electrical media, such as a RAM, ROM, NVRAM, EEPROM, flash memory, or any other digital media. The computer-readable storage media may be non-transitory in that the storage media is not an electromagnetic carrier wave. However, this does not mean that the storage media is not transportable or that it non-volatile. A programmer, such as patient programmer or clinician programmer, may also contain a more portable removable memory type to enable easy data transfer or offline data analysis.

The techniques described in this disclosure, including those attributed to IMD 14, charging device 22, or various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated, discrete, or analog logic circuitry, as well as any combinations of such components, embodied in programmers, such as physician or patient programmers, stimulators, image processing devices or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. While the techniques described herein are primarily described as being performed by processing circuitry 30 of IMD 14, processor 50 of charging device 22, or any one or more parts of the techniques described herein may be implemented by a processor of one of IMD 14, charging device 22, or another computing device, alone or in combination with each other.

In addition, any of the described units, circuitries or components may be implemented together or separately as discrete but interoperable logic devices. Depiction of different features as circuitries or units is intended to highlight different functional aspects and does not necessarily imply that such circuitries or units must be realized by separate hardware or software components. Rather, functionality associated with one or more circuitries or units may be performed by separate hardware or software components, or integrated within common or separate hardware or software components.

Various examples have been described. These and other examples are within the scope of the following claims.

What is claimed is:

1. An implantable medical device comprising:
a housing comprising an exterior surface and an interior surface;
a hybrid board within the housing;
at least one support disposed within the housing;
a temperature sensor comprising a sensor surface thermally coupled to the interior surface of the housing, wherein the temperature sensor is disposed within the housing and configured to sense a temperature of a portion of the housing;
a flexible circuit; and
at least one physically compliant material disposed between the at least one support and the temperature sensor, wherein the physically compliant material is configured to provide a physical bias against the temperature sensor and towards the interior surface of the housing, and wherein the temperature sensor is electrically coupled to the hybrid board via the flexible circuit independent of the physically compliant material.

2. The implantable medical device of claim 1, wherein the at least one physically compliant material is configured to provide the physical bias to the temperature sensor to maintain contact between the interior surface of the housing and the sensor surface of the temperature sensor.

3. The implantable medical device of claim 1, wherein the at least one support contacts at least two interior surfaces of the housing.

4. The implantable medical device of claim 1, wherein the sensor surface is an operable sensing surface and the sensing surface is disposed directly in contact with the interior surface of the housing.

5. The implantable medical device of claim 1, wherein the at least one support is in contact with the interior surface of the housing.

6. The implantable medical device of claim 1, wherein the at least one support is a rigid support.

7. The implantable medical device of claim 1, wherein the physically compliant material is an elastic pad.

8. The implantable medical device of claim 1, further comprising a thermally conductive material disposed between the sensor surface and the interior surface of the housing.

9. The implantable medical device of claim 8, wherein the housing comprises a curved inner portion, and wherein the thermally conductive material is configured to conform to the curved inner portion to couple the sensor surface and the interior surface of the housing.

10. The implantable medical device of claim 1, wherein the temperature sensor is a first temperature sensor, and wherein the implantable medical device comprises one or more additional temperature sensors disposed at multiple locations within the housing and thermally coupled to respective portions of the interior surface of the housing.

11. The implantable medical device of claim 1, wherein the housing is a titanium shield configured to protect the temperature sensor.

12. The implantable medical device of claim 1, wherein the hybrid board comprises processing circuitry configured to receive a temperature signal from the temperature sensor and control at least one function of the implantable medical device based on the temperature signal.

13. A method comprising:
attaching at least one physically compliant material with at least one support;
attaching a temperature sensor to the at least one physically compliant material;
disposing a hybrid board within a housing;
disposing the temperature sensor within the housing, the housing comprising an exterior surface and an interior surface, the housing having at least one support coupled to the housing, where the at least one physically compliant material is configured to physically bias the temperature sensor towards the interior surface of the housing with the physically compliant material;
thermally coupling the temperature sensor to the housing, the temperature sensor configured to sense a temperature of a portion of the housing, the temperature sensor including a sensor surface; and
electrically coupling the temperature sensor to the hybrid board, the temperature sensor being electrically coupled to the hybrid board via a flexible circuit independent of the physically compliant material.

14. The method of claim 13, further comprising disposing a sensing surface of the temperature sensor directly adjacent to the interior surface of the housing wherein the sensing surface is in direct contact with the interior surface of the housing.

15. The method of claim 13, further comprising disposing thermally conductive material disposed between the temperature sensor and the interior surface of the housing.

16. The method of claim 15, further comprising thermally connecting the thermally conductive material with the sensor surface and the interior surface of the housing.

17. The method of claim 13, further comprising disposing multiple temperature sensors at multiple locations within the housing, and wherein each of the multiple temperature sensors are physically biased towards the interior surface of the housing with the physically compliant material.

18. An implantable medical device comprising:
a housing comprising an exterior surface and an interior surface;
at least one support disposed within the housing;
a temperature sensor comprising a sensor surface thermally coupled to the interior surface of the housing, wherein the temperature sensor is disposed within the housing and configured to sense a temperature of a portion of the housing;

at least one physically compliant material disposed between the at least one support and the temperature 5 sensor, wherein the physically compliant material is configured to provide a physical bias against the temperature sensor and towards the interior surface of the housing;

a hybrid board disposed within the housing; 10 a flexible circuit electrically coupling the temperature sensor to the hybrid board; and processing circuitry configured to receive a temperature signal from the temperature sensor and control at least one function of the implantable medical device based 15 on the temperature signal.

* * * * *